US011931559B2

(12) United States Patent
Sherman et al.

(10) Patent No.: US 11,931,559 B2
(45) Date of Patent: Mar. 19, 2024

(54) SYSTEMS AND METHODS FOR MIXING SYRINGE VALVE ASSEMBLIES

(71) Applicant: TOLMAR INTERNATIONAL LIMITED, Dublin (IE)

(72) Inventors: James Sherman, Timnath, CO (US); Casey Dean, Fort Collins, CO (US); Carl Hart, Lakewood, CO (US); John Bingham, Elizabeth, CO (US); Hossam Aboudagher, Milliken, CO (US)

(73) Assignee: TOLMAR INTERNATIONAL LIMITED, Dublin (IE)

( * ) Notice: Subject to any disclaimer, the term of this patent is extended or adjusted under 35 U.S.C. 154(b) by 0 days.

(21) Appl. No.: 18/233,193

(22) Filed: Aug. 11, 2023

(65) Prior Publication Data
US 2023/0381422 A1    Nov. 30, 2023

Related U.S. Application Data

(63) Continuation of application No. 17/854,769, filed on Jun. 30, 2022, now Pat. No. 11,771,841, which is a continuation of application No. PCT/IB2021/062218, filed on Dec. 22, 2021.

(60) Provisional application No. 63/130,144, filed on Dec. 23, 2020.

(51) Int. Cl.
*A61M 5/315* (2006.01)
*A61J 1/20* (2006.01)
*A61M 5/19* (2006.01)

(52) U.S. Cl.
CPC ........ *A61M 5/31596* (2013.01); *A61J 1/2089* (2013.01); *A61M 5/19* (2013.01)

(58) Field of Classification Search
CPC .......... A61M 5/31596; A61M 5/19; A61M 39/1011; A61M 39/1055; A61M 39/22; A61J 1/2089; A61J 1/2051; A61J 1/2096
See application file for complete search history.

(56) References Cited

U.S. PATENT DOCUMENTS

| 4,464,174 A | 8/1984 | Ennis |
| 4,543,094 A | 9/1985 | Barnwell |
| 4,549,554 A | 10/1985 | Markham |
| 5,286,257 A | 2/1994 | Fischer |
| 5,445,614 A | 8/1995 | Haber et al. |
| 5,674,195 A | 10/1997 | Truthan |

(Continued)

FOREIGN PATENT DOCUMENTS

| AP | 2014007377 | 6/2012 |
| AT | 489991 | 12/2010 |

(Continued)

OTHER PUBLICATIONS

U.S. Appl. No. 29/843,616, filed Jun. 22, 2022, Dean et al.

(Continued)

*Primary Examiner* — Theodore J Stigell
(74) *Attorney, Agent, or Firm* — Sheridan Ross P.C.

(57) ABSTRACT

A syringe mixing system is provided for housing and mixing contents between at least two syringes. In some embodiments, a syringe coupler is provided that receives first and second syringes and includes a valve member that is convertible between a closed position and an open position. Retention systems for preventing or inhibiting removal of at least one syringe after use are also provided.

19 Claims, 18 Drawing Sheets

(56) References Cited

U.S. PATENT DOCUMENTS

| | | |
|---|---|---|
| 6,349,850 B1 | 2/2002 | Cheikh |
| 6,565,874 B1 | 5/2003 | Dunn et al. |
| 6,602,223 B2 | 8/2003 | Szapiro |
| 6,685,922 B2 | 2/2004 | Peterson |
| 6,729,370 B2 | 5/2004 | Norton et al. |
| 6,779,566 B2 | 8/2004 | Engel |
| 6,817,987 B2 | 11/2004 | Vetter et al. |
| 7,081,109 B2 | 7/2006 | Tighe et al. |
| 7,128,105 B2 | 10/2006 | Tribble et al. |
| 7,670,326 B2 | 3/2010 | Shemesh |
| 7,731,065 B2 | 6/2010 | Ingram et al. |
| 7,776,011 B2 | 8/2010 | Tennican et al. |
| 7,789,862 B2 | 9/2010 | Thorne, Jr. |
| 7,951,108 B2 | 5/2011 | Harper et al. |
| 8,002,737 B2 | 8/2011 | Tennican |
| 8,100,853 B2 | 1/2012 | Glynn |
| 8,337,557 B2 | 12/2012 | Collins et al. |
| 8,470,359 B2 | 6/2013 | Dunn |
| 8,834,449 B2 | 9/2014 | Machan et al. |
| 9,016,925 B2 | 4/2015 | Faccioli et al. |
| 9,220,577 B2 | 12/2015 | Jessop et al. |
| 9,289,562 B2 | 3/2016 | Thorne, Jr. et al. |
| 9,522,098 B2 | 12/2016 | Tuckwell et al. |
| 9,586,008 B2 | 3/2017 | Shetty et al. |
| 9,592,343 B2 | 3/2017 | Shetty et al. |
| 9,597,454 B2 | 3/2017 | Wetzel et al. |
| 9,833,558 B2 | 12/2017 | Anderson et al. |
| 9,872,962 B2 | 1/2018 | Granelli |
| 9,873,098 B2 | 1/2018 | Asada et al. |
| 9,962,492 B2 | 5/2018 | Anderson et al. |
| 10,046,154 B2 | 8/2018 | Fangrow et al. |
| 10,080,882 B2 | 9/2018 | Ekman et al. |
| 10,194,964 B2 | 2/2019 | Schlachter et al. |
| 10,278,897 B2 | 5/2019 | David et al. |
| 10,285,907 B2 | 5/2019 | David et al. |
| 10,322,235 B2 | 6/2019 | Thorne, Jr. et al. |
| D863,546 S | 10/2019 | Converse et al. |
| 10,485,930 B2 | 11/2019 | Tennican et al. |
| 10,524,983 B2 | 1/2020 | Tennican |
| 10,653,837 B2 | 5/2020 | Larsen |
| 10,669,063 B2 | 6/2020 | Stratis et al. |
| 10,703,532 B2 | 7/2020 | Stratis et al. |
| 10,864,139 B2 | 12/2020 | Genosar |
| 10,898,651 B2 | 1/2021 | Wetzel et al. |
| 10,918,796 B2 | 2/2021 | Larsen et al. |
| D948,034 S | 4/2022 | Converse et al. |
| 2001/0037091 A1 | 11/2001 | Wironen et al. |
| 2003/0180262 A1 | 9/2003 | Wironen et al. |
| 2003/0225378 A1* | 12/2003 | Wilkie ............ A61B 17/00491 604/221 |
| 2007/0255204 A1 | 11/2007 | McLean et al. |
| 2008/0124397 A1 | 5/2008 | Wironen et al. |
| 2008/0150281 A1 | 6/2008 | Rome et al. |
| 2008/0167621 A1 | 7/2008 | Wagner et al. |
| 2010/0030111 A1 | 2/2010 | Perriere |
| 2010/0121271 A1 | 5/2010 | Perriere |
| 2013/0018326 A1 | 1/2013 | Hooven et al. |
| 2013/0178823 A1 | 7/2013 | Buchine et al. |
| 2013/0274656 A1 | 10/2013 | Dehan et al. |
| 2014/0195704 A1 | 7/2014 | Bhatia et al. |
| 2014/0251438 A1 | 9/2014 | Gettings et al. |
| 2014/0261082 A1 | 9/2014 | Anderson et al. |
| 2014/0276385 A1 | 9/2014 | Buchine et al. |
| 2014/0323970 A1 | 10/2014 | Duncan |
| 2015/0174336 A1 | 6/2015 | Buchine et al. |
| 2015/0204451 A1 | 7/2015 | Wattellier et al. |
| 2015/0217058 A1 | 8/2015 | Hooven et al. |
| 2015/0219099 A1 | 8/2015 | Wattellier et al. |
| 2015/0231334 A1 | 8/2015 | Buchine et al. |
| 2015/0367072 A1 | 12/2015 | Constantineau et al. |
| 2015/0367073 A1 | 12/2015 | Standley et al. |
| 2015/0374917 A1 | 12/2015 | Standley et al. |
| 2015/0374925 A1 | 12/2015 | Standley et al. |
| 2016/0120527 A1 | 5/2016 | Larsen et al. |
| 2016/0144105 A1 | 5/2016 | Hooven et al. |
| 2016/0160854 A1 | 6/2016 | Dehan et al. |
| 2016/0195074 A1 | 7/2016 | Beard et al. |
| 2016/0220764 A1 | 8/2016 | Durvasula et al. |
| 2016/0243060 A1 | 8/2016 | Standley et al. |
| 2016/0263320 A1 | 9/2016 | Constantineau et al. |
| 2016/0331682 A1 | 11/2016 | Payet-Burin |
| 2017/0100541 A1 | 4/2017 | Constantineau et al. |
| 2017/0135903 A1 | 5/2017 | Wattellier et al. |
| 2017/0144118 A1 | 5/2017 | Gettings et al. |
| 2017/0189619 A1 | 7/2017 | Constantineau et al. |
| 2017/0196771 A1 | 7/2017 | Hooven et al. |
| 2017/0209642 A1 | 7/2017 | Hooven et al. |
| 2017/0232196 A1 | 8/2017 | Constantineau et al. |
| 2017/0232197 A1 | 8/2017 | Standley et al. |
| 2017/0259007 A1 | 9/2017 | Standley et al. |
| 2018/0043107 A1 | 2/2018 | Hooven et al. |
| 2018/0099095 A1 | 4/2018 | Standley et al. |
| 2018/0110922 A1 | 4/2018 | Dunki-Jacobs et al. |
| 2018/0110928 A1 | 4/2018 | Constantineau et al. |
| 2018/0110931 A1 | 4/2018 | Standley et al. |
| 2018/0126076 A1 | 5/2018 | Constantineau et al. |
| 2018/0140774 A1 | 5/2018 | Constantineau et al. |
| 2018/0161497 A1 | 6/2018 | Hooven et al. |
| 2018/0161501 A1 | 6/2018 | Standley et al. |
| 2018/0207369 A1 | 7/2018 | Converse et al. |
| 2018/0221574 A1 | 8/2018 | Dunki-Jacobs et al. |
| 2019/0167910 A1 | 6/2019 | Buchine et al. |
| 2019/0240407 A1 | 8/2019 | Constantineau et al. |
| 2019/0275250 A1 | 9/2019 | Constantineau et al. |
| 2019/0350592 A1 | 11/2019 | Bagaoisan et al. |
| 2019/0374726 A1 | 12/2019 | Durvasula et al. |
| 2020/0061292 A1 | 2/2020 | Dunki-Jacobs et al. |
| 2020/0139048 A1 | 5/2020 | Buchine et al. |
| 2020/0146938 A1 | 5/2020 | Bourelle et al. |
| 2020/0147314 A1 | 5/2020 | Howlett et al. |
| 2020/0214625 A1 | 7/2020 | Hooven et al. |
| 2020/0316290 A1 | 10/2020 | Bourelle et al. |
| 2020/0338257 A1 | 10/2020 | Hooven et al. |
| 2020/0338258 A1 | 10/2020 | Standley et al. |
| 2021/0145697 A1 | 5/2021 | Bourelle et al. |
| 2021/0186813 A1 | 6/2021 | Bourelle et al. |
| 2021/0260282 A1 | 8/2021 | Dunki-Jacobs et al. |
| 2021/0268178 A1 | 9/2021 | Hooven et al. |
| 2021/0338928 A1 | 11/2021 | Hooven et al. |
| 2021/0353222 A1 | 11/2021 | Hooven et al. |
| 2021/0386621 A1 | 12/2021 | Hooven et al. |
| 2022/0001112 A1 | 1/2022 | Chagnon et al. |
| 2022/0184312 A1 | 6/2022 | Wattellier et al. |
| 2022/0331523 A1 | 10/2022 | Sherman et al. |

FOREIGN PATENT DOCUMENTS

| | | |
|---|---|---|
| AU | 2007324478 | 5/2008 |
| AU | 2008219304 | 8/2008 |
| AU | 2011346979 | 7/2013 |
| AU | 2013294886 | 1/2015 |
| AU | 2014232211 | 10/2015 |
| AU | 2014281715 | 1/2016 |
| AU | 2014294854 | 2/2016 |
| AU | 2014294901 | 2/2016 |
| AU | 2014294902 | 2/2016 |
| AU | 2014364433 | 8/2016 |
| AU | 2015212986 | 8/2016 |
| AU | 2015305635 | 4/2017 |
| AU | 2015305636 | 4/2017 |
| AU | 2015305638 | 4/2017 |
| AU | 2015305641 | 4/2017 |
| AU | 2015364280 | 7/2017 |
| AU | 2017014274 | 8/2017 |
| AU | 2017014275 | 8/2017 |
| AU | 2016235138 | 10/2017 |
| AU | 2016266657 | 11/2017 |
| AU | 2016296096 | 1/2018 |
| AU | 2016306797 | 2/2018 |
| AU | 2018200957 | 8/2018 |
| AU | 2018278883 | 1/2019 |
| AU | 2019200849 | 2/2019 |
| AU | 2019203236 | 5/2019 |
| AU | 2018230507 | 10/2019 |

(56) References Cited

FOREIGN PATENT DOCUMENTS

| | | |
|---|---|---|
| AU | 2018271998 | 12/2019 |
| AU | 2018285530 | 1/2020 |
| AU | 2018347573 | 4/2020 |
| AU | 2018352580 | 4/2020 |
| AU | 2020202709 | 5/2020 |
| AU | 2021200878 | 3/2021 |
| AU | 2019364364 | 5/2021 |
| AU | 2019419507 | 8/2021 |
| AU | 2020316106 | 2/2022 |
| AU | 2022200891 | 3/2022 |
| BR | PI0719149 | 2/2014 |
| BR | PI0807713 | 6/2014 |
| BR | 112015001330 | 7/2017 |
| BR | 112013015995 | 7/2018 |
| BR | 112020007113 | 9/2020 |
| BR | 112020007429 | 10/2020 |
| BR | 112021012996 | 9/2021 |
| CA | 2670206 | 5/2008 |
| CA | 2822406 | 6/2008 |
| CA | 2678523 | 8/2008 |
| CA | 2843227 | 12/2012 |
| CA | 2876056 | 1/2014 |
| CA | 2905207 | 9/2014 |
| CA | 2918927 | 1/2015 |
| CA | 2918995 | 1/2015 |
| CA | 2919004 | 1/2015 |
| CA | 2934538 | 6/2015 |
| CA | 2936721 | 7/2015 |
| CA | 2938059 | 8/2015 |
| CA | 2994801 | 2/2016 |
| CA | 2994802 | 2/2016 |
| CA | 2994803 | 2/2016 |
| CA | 2994804 | 2/2016 |
| CA | 2971440 | 6/2016 |
| CA | 3032681 | 6/2016 |
| CA | 2980585 | 9/2016 |
| CA | 3019104 | 12/2016 |
| CA | 2991441 | 1/2017 |
| CA | 2994300 | 2/2017 |
| CA | 2994386 | 8/2018 |
| CA | 3055922 | 9/2018 |
| CA | 175996 | 11/2018 |
| CA | 183851 | 11/2018 |
| CA | 3064324 | 11/2018 |
| CA | 3066471 | 12/2018 |
| CA | 3078633 | 4/2019 |
| CA | 3078964 | 4/2019 |
| CA | 3077095 | 5/2019 |
| CA | 3117324 | 4/2020 |
| CA | 3125287 | 7/2020 |
| CA | 3146856 | 1/2021 |
| CN | 101553266 | 10/2009 |
| CN | 101616709 | 12/2009 |
| CN | 103402619 | 11/2013 |
| CN | 104379977 | 2/2015 |
| CN | 105407943 | 3/2016 |
| CN | 105551476 | 4/2016 |
| CN | 105556119 | 5/2016 |
| CN | 105612346 | 5/2016 |
| CN | 106061253 | 10/2016 |
| CN | 106132379 | 11/2016 |
| CN | 106163501 | 11/2016 |
| CN | 106573111 | 4/2017 |
| CN | 106794305 | 5/2017 |
| CN | 107073201 | 8/2017 |
| CN | 107106771 | 8/2017 |
| CN | 107205938 | 9/2017 |
| CN | 107580489 | 1/2018 |
| CN | 107921208 | 4/2018 |
| CN | 108289998 | 7/2018 |
| CN | 108290000 | 7/2018 |
| CN | 108404261 | 8/2018 |
| CN | 110464917 | 11/2019 |
| CN | 110996876 | 4/2020 |
| CN | 111132710 | 5/2020 |
| CN | 111344064 | 6/2020 |
| CN | 111601578 | 8/2020 |
| CN | 111629703 | 9/2020 |
| CN | 111655313 | 9/2020 |
| CN | 1118033762 | 10/2020 |
| CN | 112245287 | 1/2021 |
| CN | 113230486 | 8/2021 |
| CN | 113613616 | 11/2021 |
| CN | 113645935 | 11/2021 |
| CN | 114450047 | 5/2022 |
| DK | 2125099 | 3/2011 |
| DK | 2654938 | 11/2014 |
| DK | 3010568 | 5/2019 |
| DK | 2723426 | 11/2019 |
| DK | 3274020 | 4/2021 |
| EP | 1391219 | 2/2004 |
| EP | 2094340 | 9/2009 |
| EP | 2121112 | 11/2009 |
| EP | 2125099 | 12/2009 |
| EP | 2331190 | 6/2011 |
| EP | 2376141 | 10/2011 |
| EP | 2438339 | 4/2012 |
| EP | 2654938 | 10/2013 |
| EP | 2723426 | 4/2014 |
| EP | 2877763 | 6/2015 |
| EP | 2902002 | 8/2015 |
| EP | 2968770 | 1/2016 |
| EP | 3010568 | 4/2016 |
| EP | 3025056 | 6/2016 |
| EP | 3025057 | 6/2016 |
| EP | 3025058 | 6/2016 |
| EP | 3035903 | 6/2016 |
| EP | 3082419 | 10/2016 |
| EP | 3099282 | 12/2016 |
| EP | 3183015 | 6/2017 |
| EP | 3183016 | 6/2017 |
| EP | 3183019 | 6/2017 |
| EP | 3183020 | 6/2017 |
| EP | 3233061 | 10/2017 |
| EP | 3268068 | 1/2018 |
| EP | 3274020 | 1/2018 |
| EP | 3313478 | 5/2018 |
| EP | 3325049 | 5/2018 |
| EP | 3592405 | 1/2020 |
| EP | 3634357 | 4/2020 |
| EP | 3638186 | 4/2020 |
| EP | 3682920 | 7/2020 |
| EP | 3694582 | 8/2020 |
| EP | 3697367 | 8/2020 |
| EP | 3706909 | 9/2020 |
| EP | 3870132 | 9/2021 |
| EP | 3890805 | 10/2021 |
| EP | 3906002 | 11/2021 |
| EP | 3909623 | 11/2021 |
| EP | 4003459 | 6/2022 |
| ES | 2357478 | 4/2011 |
| ES | 2524695 | 12/2014 |
| ES | 2597736 | 1/2017 |
| ES | 2627978 | 8/2017 |
| ES | 2629412 | 8/2017 |
| ES | 2644817 | 11/2017 |
| ES | 2656768 | 2/2018 |
| ES | 2728054 | 10/2019 |
| ES | 2753031 | 4/2020 |
| ES | 2784517 | 9/2020 |
| ES | 2784680 | 9/2020 |
| ES | 2867775 | 10/2021 |
| FR | 2909001 | 5/2008 |
| FR | 2912919 | 8/2008 |
| FR | 2933872 | 1/2010 |
| FR | 2934500 | 2/2010 |
| FR | 2936160 | 3/2010 |
| FR | 2946408 | 12/2010 |
| FR | 2969507 | 6/2012 |
| FR | 2993791 | 1/2014 |
| FR | 2998365 | 5/2014 |
| FR | 3008744 | 1/2015 |
| FR | 3008745 | 1/2015 |
| FR | 3008746 | 1/2015 |

(56) References Cited

FOREIGN PATENT DOCUMENTS

| | | |
|---|---|---|
| FR | 3092001 | 7/2020 |
| FR | 3106765 | 8/2021 |
| FR | 3106865 | 8/2021 |
| FR | 3110392 | 11/2021 |
| HU | E043627 | 9/2019 |
| HU | E054394 | 9/2021 |
| IL | 198849 | 6/2011 |
| IL | 200263 | 7/2013 |
| IN | 201717008723 | 7/2017 |
| IN | 201717008752 | 7/2017 |
| IN | 201717008825 | 8/2017 |
| IN | 201717008826 | 8/2017 |
| IN | 201717025457 | 11/2017 |
| IN | 201717040205 | 12/2017 |
| IN | 201817003834 | 4/2018 |
| JP | 2010-510012 | 4/2010 |
| JP | 2010-518951 | 6/2010 |
| JP | 5093822 | 12/2012 |
| JP | 5143849 | 2/2013 |
| JP | 2014-503280 | 2/2014 |
| JP | 2014-523296 | 9/2014 |
| JP | 6560187 | 9/2014 |
| JP | 5755164 | 7/2015 |
| JP | 2015-524303 | 8/2015 |
| JP | 5882358 | 3/2016 |
| JP | 2016-512148 | 4/2016 |
| JP | 2016-524513 | 8/2016 |
| JP | 2016-525182 | 8/2016 |
| JP | 2016-525645 | 8/2016 |
| JP | 2016-525647 | 8/2016 |
| JP | 2017-503017 | 1/2017 |
| JP | 2017-504430 | 2/2017 |
| JP | 6122496 | 4/2017 |
| JP | 2017-525469 | 9/2017 |
| JP | 2017-525470 | 9/2017 |
| JP | 2017-525471 | 9/2017 |
| JP | 2017-525472 | 9/2017 |
| JP | 2017-538731 | 12/2017 |
| JP | 2018-509252 | 4/2018 |
| JP | 6345590 | 6/2018 |
| JP | 2018-517536 | 7/2018 |
| JP | 2018-522654 | 8/2018 |
| JP | 2018-522684 | 8/2018 |
| JP | 2018-153672 | 10/2018 |
| JP | 6456479 | 1/2019 |
| JP | 6462859 | 1/2019 |
| JP | 2019-055286 | 4/2019 |
| JP | 2019-065043 | 4/2019 |
| JP | 6525445 | 6/2019 |
| JP | 6580777 | 9/2019 |
| JP | 2019-166407 | 10/2019 |
| JP | 2019-188174 | 10/2019 |
| JP | 6594410 | 10/2019 |
| JP | 2019-195670 | 11/2019 |
| JP | 6606274 | 11/2019 |
| JP | 2019-217323 | 12/2019 |
| JP | 6616840 | 12/2019 |
| JP | 2020-032240 | 3/2020 |
| JP | 2020-510486 | 4/2020 |
| JP | 6691041 | 4/2020 |
| JP | 2020-110665 | 7/2020 |
| JP | 2020-521540 | 7/2020 |
| JP | 2020-523131 | 8/2020 |
| JP | 2020-536658 | 12/2020 |
| JP | 2020-536660 | 12/2020 |
| JP | 2021-063134 | 4/2021 |
| JP | 2021-510550 | 4/2021 |
| JP | 2021-073311 | 5/2021 |
| JP | 2021-130002 | 5/2021 |
| JP | 6882377 | 6/2021 |
| JP | 2021-191465 | 12/2021 |
| JP | 2022-024075 | 2/2022 |
| JP | 2022-512039 | 2/2022 |
| JP | 7000443 | 2/2022 |
| JP | 2022-516608 | 3/2022 |
| JP | 7030762 | 3/2022 |
| JP | 7036910 | 3/2022 |
| JP | 7053709 | 4/2022 |
| JP | 2022-068324 | 5/2022 |
| JP | 7063920 | 5/2022 |
| JP | 2022-084917 | 6/2022 |
| JP | 2022-101639 | 7/2022 |
| KR | 2009-0076984 | 7/2009 |
| KR | 2009-0113866 | 11/2009 |
| KR | 101070203 | 10/2011 |
| KR | 101213003 | 12/2012 |
| KR | 2013-0133255 | 12/2013 |
| KR | 2016-0033131 | 3/2016 |
| KR | 2016-0045710 | 4/2016 |
| KR | 2016-0045711 | 4/2016 |
| KR | 2016-0135182 | 11/2016 |
| KR | 101871701 | 7/2018 |
| KR | 101882723 | 7/2018 |
| PL | 2125099 | 3/2011 |
| TW | 200836786 | 9/2008 |
| TW | 200902109 | 1/2009 |
| TW | I417117 | 12/2013 |
| WO | WO 96/036429 | 11/1996 |
| WO | WO 02/067814 | 9/2002 |
| WO | WO 2008/051925 | 5/2008 |
| WO | WO 2008/062032 | 5/2008 |
| WO | WO 2008/101892 | 8/2008 |
| WO | WO 2010/007296 | 1/2010 |
| WO | WO 2010/015770 | 2/2010 |
| WO | WO 2010/031974 | 3/2010 |
| WO | WO 2010/139913 | 12/2010 |
| WO | WO 2012/085428 | 6/2012 |
| WO | WO 2014/016479 | 1/2014 |
| WO | WO 2014/076419 | 5/2014 |
| WO | WO 2014/145959 | 9/2014 |
| WO | WO 2014/146060 | 9/2014 |
| WO | WO 2015/009871 | 1/2015 |
| WO | WO 2015/011352 | 1/2015 |
| WO | WO 2015/011353 | 1/2015 |
| WO | WO 2015/011384 | 1/2015 |
| WO | WO 2015/095624 | 6/2015 |
| WO | WO 2015/107214 | 7/2015 |
| WO | WO 2015/113897 | 8/2015 |
| WO | WO 2016/028814 | 2/2016 |
| WO | WO 2016/028815 | 2/2016 |
| WO | WO 2016/028817 | 2/2016 |
| WO | WO 2016/028820 | 2/2016 |
| WO | WO 2016/100949 | 6/2016 |
| WO | WO 2016/166339 | 10/2016 |
| WO | WO 2016/190980 | 12/2016 |
| WO | WO 2017/014847 | 1/2017 |
| WO | WO 2017/027876 | 2/2017 |
| WO | WO 2017/062005 | 4/2017 |
| WO | WO 2018/085318 | 5/2018 |
| WO | WO 2018/165588 | 9/2018 |
| WO | WO 2018/218082 | 11/2018 |
| WO | WO 2018/232171 | 12/2018 |
| WO | WO 2019/011870 | 1/2019 |
| WO | WO 2019/075337 | 4/2019 |
| WO | WO 2019/079335 | 4/2019 |
| WO | WO 2019/094547 | 5/2019 |
| WO | WO 2020/086581 | 4/2020 |
| WO | WO 2020/142544 | 7/2020 |
| WO | WO 2020/152424 | 7/2020 |
| WO | WO 2020/180081 | 9/2020 |
| WO | WO 2020/180507 | 9/2020 |
| WO | WO 2020/217170 | 10/2020 |
| WO | WO 2020/240417 | 12/2020 |
| WO | WO 2021/016567 | 1/2021 |
| WO | WO 2021/156573 | 8/2021 |
| WO | WO 2021/156574 | 8/2021 |
| WO | WO 2021/234306 | 11/2021 |
| WO | WO 2021/243341 | 12/2021 |

(56) References Cited

FOREIGN PATENT DOCUMENTS

| WO | WO 2022/006063 | 1/2022 |
|---|---|---|
| WO | WO 2022/031784 | 2/2022 |

OTHER PUBLICATIONS

International Search Report and Written Opinion for International (PCT) Patent Application No. PCT/IB2021/062218, dated Apr. 7, 2022, 18 pages.
International Preliminary Report on Patentability for International (PCT) Patent Application No. PCT/IB2021/062218, dated Jul. 6, 2023, 13 pages.
Article 94(3) Communication for Europe Patent Application No. 21840159.4, dated Jan. 31, 2023, 10 pages.
Article 94(3) Communication for Europe Patent Application No. 21840159.4, dated Jul. 28, 2023, 8 pages.
Official Action for U.S. Appl. No. 17/854,769, dated Jan. 24, 2023, 14 pages.
Official Action for U.S. Appl. No. 17/854,769, dated May 16, 2023, 6 pages.
Notice of Allowance for U.S. Appl. No. 17/854,769, dated Jul. 18, 2023, 8 pages.

\* cited by examiner

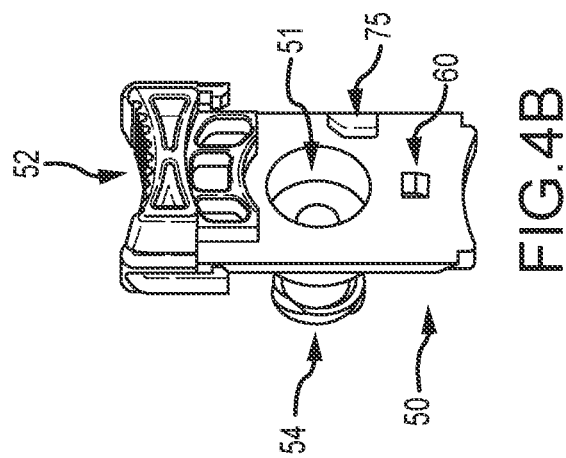
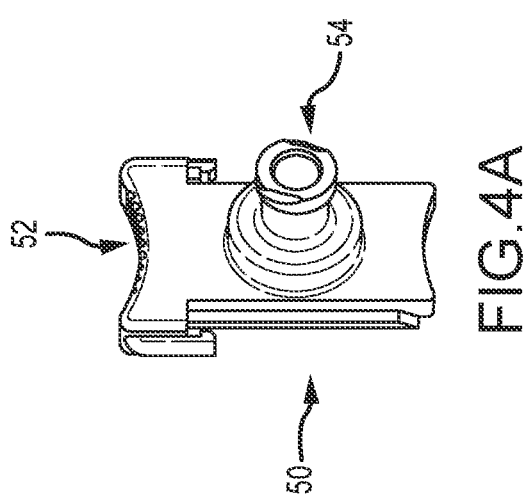
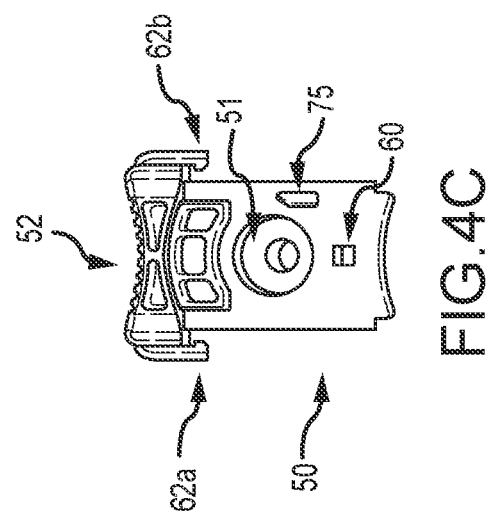

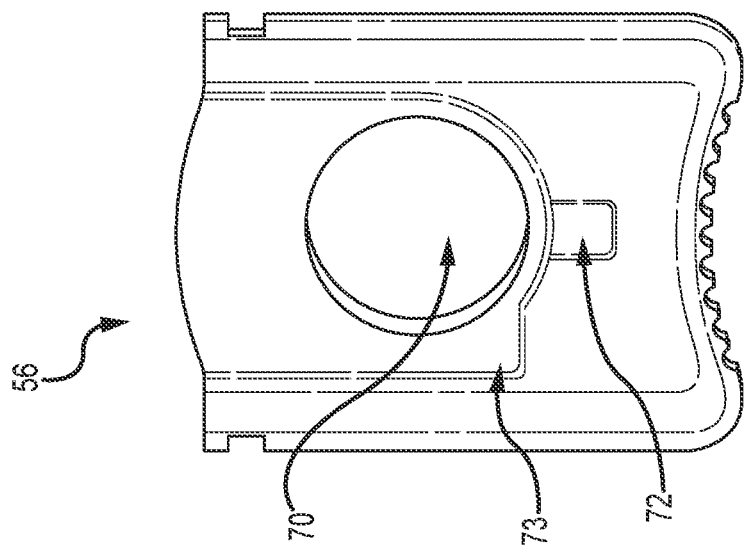
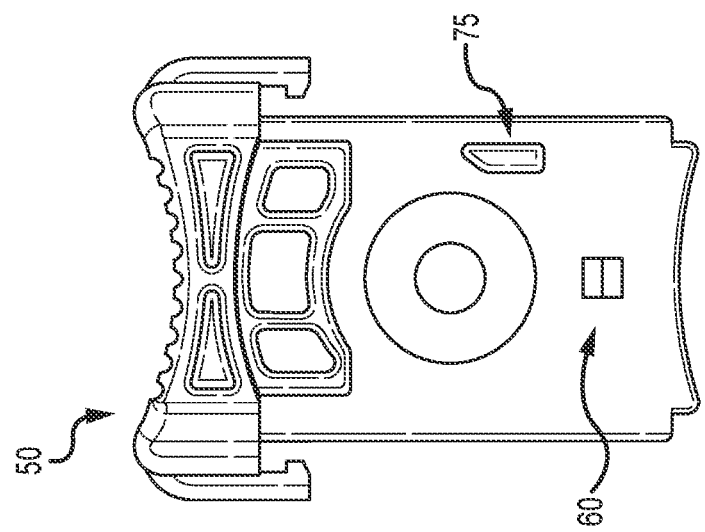
FIG.9

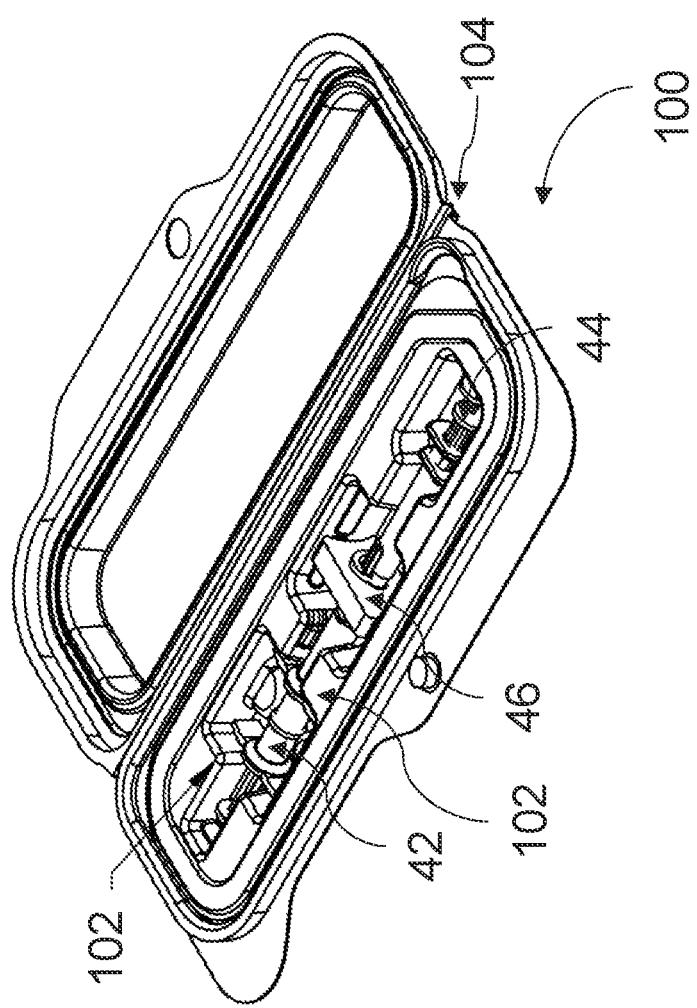

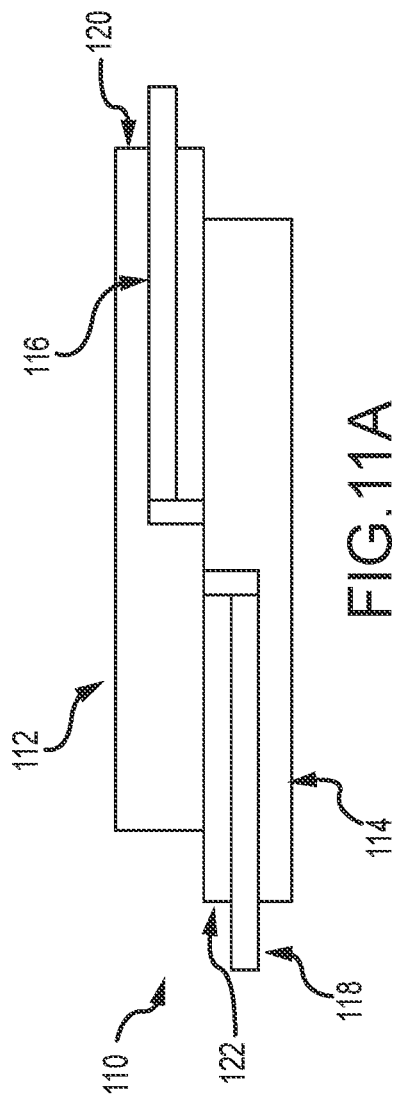
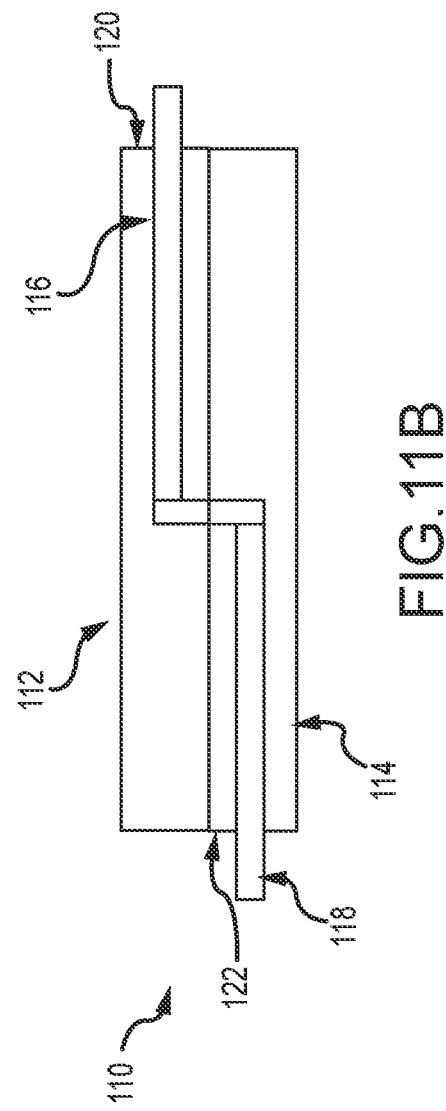
FIG. 11A
FIG. 11B

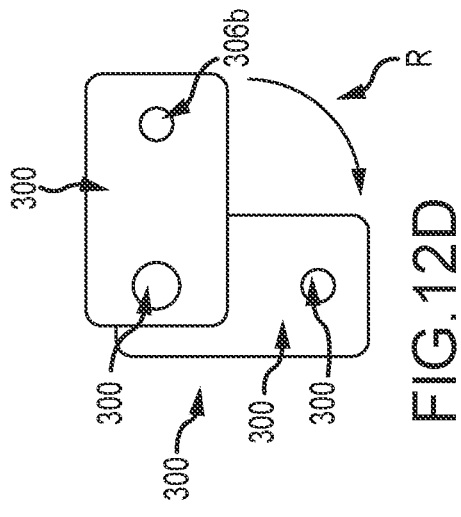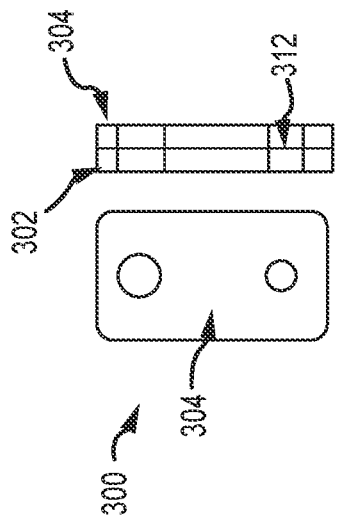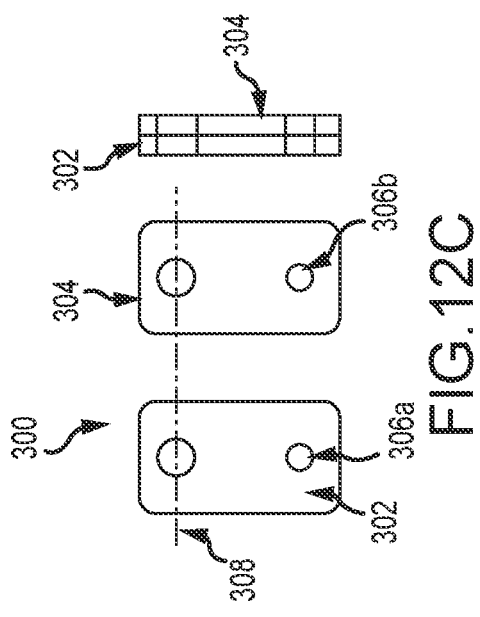

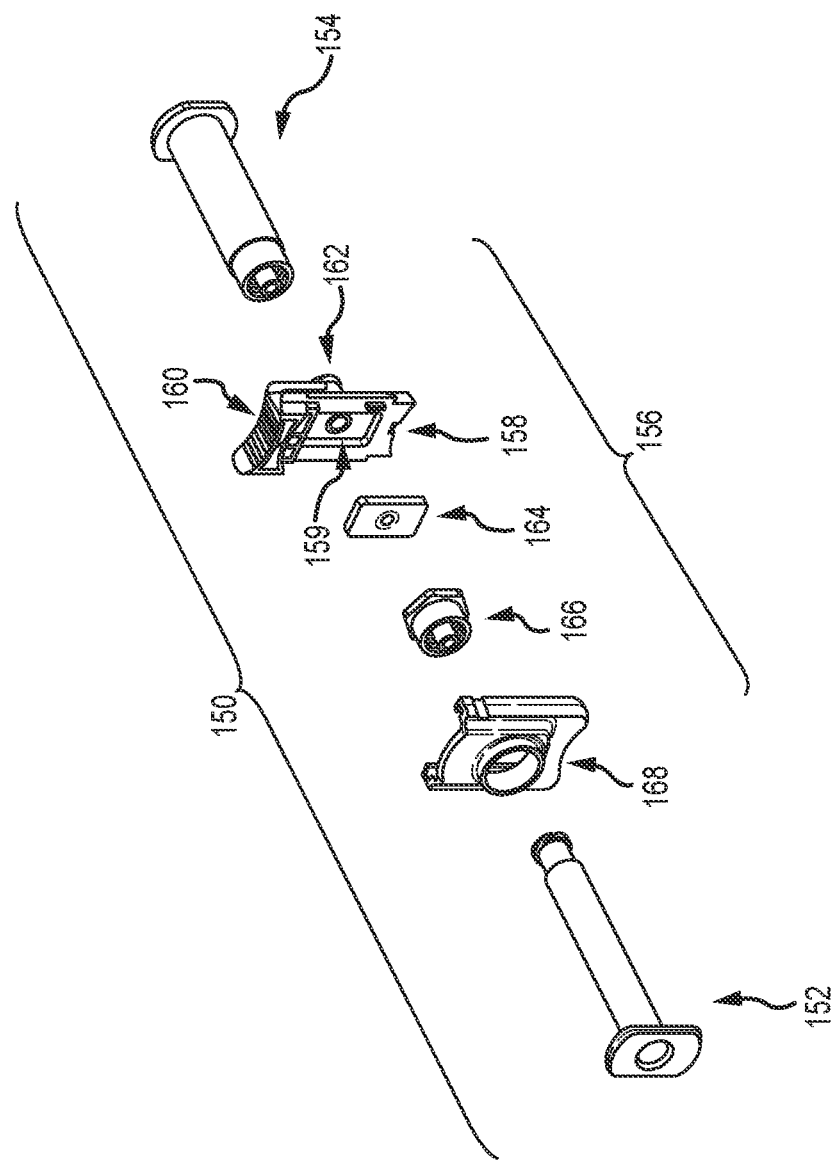

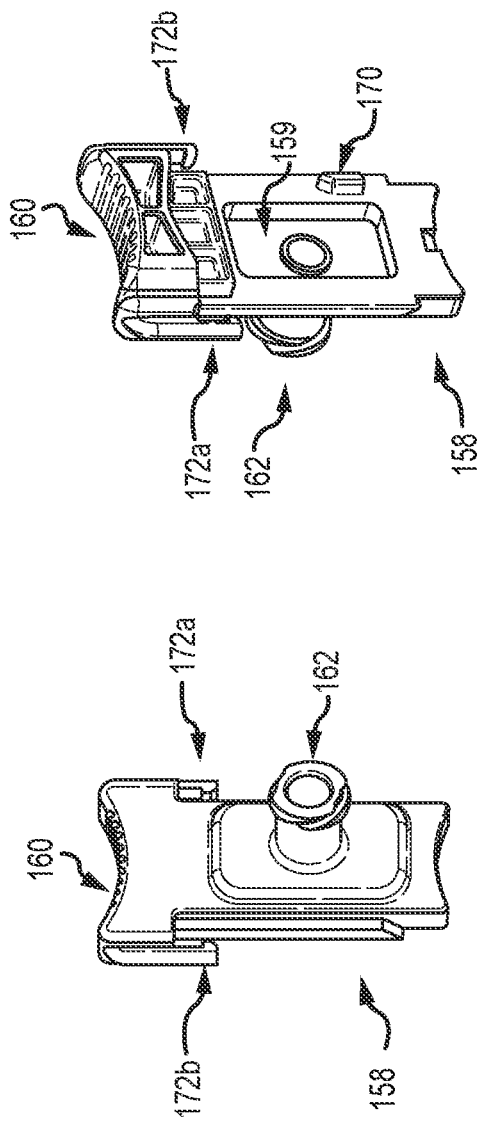
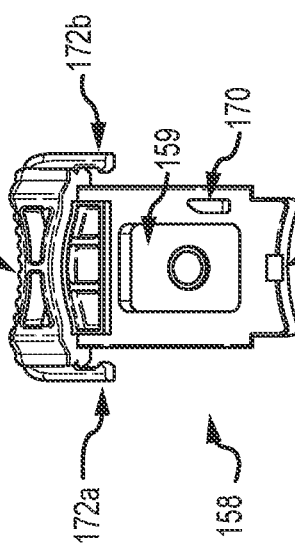
FIG. 14A
FIG. 14B
FIG. 14C

SYSTEMS AND METHODS FOR MIXING SYRINGE VALVE ASSEMBLIES

This U.S. Non-Provisional Patent Application is a Continuation of and claims the benefit of priority of U.S. patent application Ser. No. 17/854,769, filed on Jun. 30, 2022, which claims benefit of International Application PCT/IB2021/062218, filed Dec. 22, 2021, and claims the benefit of priority of U.S. Provisional Patent Application Ser. No. 63/130,144, filed on Dec. 23, 2020, the entire disclosures of which are hereby incorporated by reference.

FIELD

The present disclosure relates generally to systems for mixing and to mixing syringes. More specifically, embodiments of the present disclosure relate to mixing syringes operable to store and selectively mix contents between two syringes, and which include a valve assembly to separate syringe contents at least prior to mixing operations.

BACKGROUND

It is known to store drugs and therapeutic agents in a lyophilized or powdered form. For example, because of stability and shelf-life factors, therapeutic proteins are often formulated as powders that must be reconstituted, e.g. in a liquid or flowable medium or material, prior to injection. Similarly, it is known to store components of certain complex drug formulations (whether liquid or solid) in separate containers for reasons related to stability or reactivity of the components, where the contents of the separate containers must be mixed prior to injection. Related methods and systems have been provided to allow users and healthcare professionals to combine and formulate a drug just prior to administration. Known systems and methods include single-barrel systems such as those shown and described in U.S. Pat. No. 9,592,343 to Shetty et al., which is hereby incorporated by reference. Such systems and methods generally comprise two or more contents initially separated by a valved stopper or similar member and wherein repetitive motion of the stopper and associated plunger rod is operable to mix syringe contents and subsequently eject a solution from the device. Dual-syringe systems and methods are also known, such as those shown and described in U.S. Pat. No. 9,220,577 to Jessop et al, which is hereby incorporated by reference in its entirety. Dual-syringe systems generally comprise a first material provided in a first syringe barrel and a second material provided in a second syringe barrel. The two syringe barrels of such systems can be connected to one another by joining their distal outlets such that the two syringes are in fluid communication. Sequential activation of the plunger rods of each syringe is then operable to force contents between the two syringes and provide a mixing action.

However, various known systems and devices suffer from drawbacks including, for example, a high level of pre-administration steps that can increase the likelihood of user error, improper mixing, dosing errors, and unwanted migration or leakage of syringe contents. For example, existing devices may initially be provided to a user as two separate syringes, each housing separate contents, e.g. a liquid or flowable component and a lyophilizate or other form of therapeutic agent, in order to reduce or eliminate the risk of unwanted migration of the liquid or flowable component from a first syringe to the lyophilizate or other form of therapeutic agent of a second syringe during storage. However, the use of such a device requires additional steps, including assembly steps, before mixing and administration can occur. Conversely, single-barrel systems reduce or eliminate the need to connect or assemble components prior to mixing but provide for the possibility that a liquid or flowable component can migrate or leak into a volume containing lyophilizate or other form of therapeutic agent prior to the desired time for mixing. Single-barrel systems are also restricted by the viscosity of syringe contents and are not suitable for all applications.

SUMMARY

Accordingly, there has been a long-felt and unmet need to provide methods and systems for mixing drugs and therapeutic agents while reducing the risks and drawbacks of methods and systems of the prior art.

It is an object of the present disclosure to provide methods and systems for mixing contents while reducing the number of required administration steps. It is also an object of the present disclosure to provide methods and systems for mixing contents which reduce the risk of adverse user errors and mistakes associated with administration of said contents. It is a further object of the present disclosure to provide methods and systems for mixing the contents of containers, chambers, or syringes while preventing or reducing the risk of unwanted migration, combination, mixing, etc. of materials. Furthermore, it is an object of the present disclosure to provide methods and systems for mixing portions of a pharmaceutical composition or formulation comprising an active pharmaceutical ingredient (API) useful in the treatment in a disease or disorder in a patient. It is yet a further object of the present disclosure to provide methods and systems for mixing materials of a pharmaceutical formulation comprising lyophilized leuprolide or a pharmaceutically acceptable salt thereof (e.g. leuprolide acetate) and a biodegradable polymer-solvent system useful in the treatment of a disease or a disorder, including a cancer, including but not limited to prostate cancer or breast cancer.

In various embodiments, mixing syringe systems are provided comprising a first syringe, a second syringe, and a syringe coupler or coupling device. The syringe coupler is contemplated as comprising a device that is operable to interconnect the first and second syringe and to segregate contents of the two syringes during shipping and storage, for example, and which provides a reliable seal or closure element to achieve segregation while also obviating the need for users to assemble the syringes prior to mixing. In some embodiments, a first syringe, a second syringe, and a syringe coupler are provided and the components are interconnected for shipping and storage such that a user need not assemble components prior to mixing for subsequent administration of a drug or a therapeutic agent. While various embodiments of the present disclosure contemplate a first syringe comprising first syringe contents (e.g. fluid) and a second syringe comprising second syringe contents (e.g. solid(s)), further embodiments contemplate that a first syringe may be initially devoid of material and a second syringe is provided that comprises one or more contents that require mixing. It should be recognized that various storing, mixing, and reconstitution applications are contemplated by embodiments of the present disclosure and inventive aspects of the disclosure are not limited to any particular intended use or application.

In some embodiments, a user-activated element is provided with systems of the present disclosure. The user-activated element preferably comprises an irreversible "oneway" feature wherein the user is allowed to activate the element and move the element from a first state to a second state but cannot return the element to the first state. For example, in some embodiments, a valve activation element is provided that is operable to be moved by a user from a first position (e.g. a sealed position) to a second position (e.g. a flow-enabled position) but cannot perform a reverse operation to close the element (i.e. the operation from a first position to a second position is irreversible).

In various embodiments, a syringe coupler or hub member is provided wherein at least one syringe can be connected to the syringe coupler and wherein removal of the syringe from the coupler is prevented or impeded. In some embodiments, for example, a first syringe comprising a polymer is operable to be connected and/or disconnected from a syringe coupler prior to activation or adjustment of the syringe coupler. Once the syringe coupler has been activated (e.g. a fluid flow path in the coupler has been opened), the first syringe is no longer capable of being removed. Preventing removal of at least one syringe from the coupler is useful, for example, to guide the user in the use of a second syringe (and only a second syringe) during administration once mixing is completed.

In various embodiments, systems and devices of the present disclosure comprise an elastomer element operable to seal a fluid pathway between first and second syringes. It is contemplated that devices and systems of the present disclosure are suitable for housing various materials and agents including, but not limited to: drugs and other therapeutic agents (in solid, e.g. lyophilized, or semi-solid or liquid/fluid form); liquid or flowable diluents, excipients or solvent systems; solvent systems further comprising co-solvents, polymer-solvent systems; polymer-solvent systems comprising co-polymers; or any combination thereof. A non-limiting example of a solvent suitable for use in the systems and devices of the present disclosure is N-methyl-2-pyrrolidone (NMP), a liquid organic solvent with known volatility capable of producing gaseous vapor, which can circulate within enclosed spaces such as an inner plastic tray enclosure or outer carton commonly associated with a drug products packaging. While various embodiments of the present disclosure contemplate packaging and sealing elements with a secure seal for various materials and uses, some embodiments contemplate and provide systems that securely house NMP or similar solvent and separate the NMP from a solid such as lyophilized leuprolide acetate. NMP is allowed to migrate into a storage or housing area of the solid, the active pharmaceutical ingredient could be degraded such that shelf life and overall stability of the materials are reduced. It should be recognized that other materials and applications stand to benefit from storage and sealing elements that provide a secure seal (at least prior to mixing) and the present disclosure is not limited to NMP and/or leuprolide acetate. Embodiments of the present disclosure as shown and described herein provide for reliable physical separation and prevention of migration of vapor, liquids, and solids.

Various elastomers (e.g. santoprene) are contemplated for use with valve assemblies of embodiments of the present disclosure to inhibit or prevent liquid or gaseous solvent transmission. In further embodiments, it is contemplated that plastic components (including plastic-on-plastic components) are provided that create sufficient sealing to prevent liquid or gaseous solvent transmission between syringes and other components of the present disclosure.

While various materials are contemplated for use with embodiments of the present disclosure, preferred embodiments of the present disclosure contemplate the use of materials that are operable to withstand and are compatible with terminal manufacturing sterilization using, e.g., e-beam irradiation, gamma radiation, x-ray techniques, and ethylene oxide sterilization.

In one embodiment, a syringe-to-syringe mixing system is provided that comprises a first syringe barrel comprising a hollow body defining an internal chamber, and the hollow body has a proximal end and a distal dispensing end with an outlet. The system also comprises a second syringe barrel comprising a hollow body defining an internal chamber, the hollow body of the second syringe barrel having a proximal end and a distal dispensing end with an outlet. The first syringe band and the second syringe barrel each comprise a plunger slidably disposed within the syringe barrel for applying pressure to a content housed within the internal chambers. A syringe coupler is provided that is operable to receive the first syringe barrel and the second syringe barrel. The syringe coupler comprises a displaceable seal that comprises a flow port that is offset from the millet of at least one of the first syringe barrel and the second syringe barrel when the displaceable seal is provided in a first position, and wherein the flow port is aligned with the outlet of the first syringe barrel and the second syringe barrel when the displaceable seal is provided in a second position.

In another embodiment, a syringe-to-syringe mixing system is provided that comprises a first syringe barrel with a hollow body, the hollow body having a proximal end and a distal dispensing end with an outlet; and a second syringe barrel with a hollow body and an outlet, the second syringe comprising a distal dispensing end with an outlet. The first syringe barrel and the second syringe barrel each comprise a plunger slidably disposed within the syringe barrel for applying pressure to a material housed within the internal chambers. A valve assembly is provided that is operable to receive the first syringe barrel and the second syringe barrel. The valve assembly comprises a displaceable user-interface operable to receive a force from a user and transmit the force to a displaceable seal, and wherein the displaceable user-interface is moveable in a direction substantially perpendicular to a longitudinal axis of at least one of the first syringe barrel and the second syringe barrel.

In various embodiments, methods of mixing syringe contents and preparing therapeutic agents are provided. In one embodiment, a method of preparing a therapeutic agent is provided that comprises providing a first syringe barrel and a second syringe barrel. The first syringe barrel and the second syringe barrel each comprise a plunger slidably disposed therein for applying pressure to a material housed within the syringe barrels. A syringe coupler is provided that is operable to receive the first syringe barrel and the second syringe barrel, and the syringe coupler comprises a user-interface and a displaceable seal. The method comprises securing at least one of the first syringe barrel and the second syringe barrel to the syringe coupler, applying a force to the user-interface to move the displaceable seal from a first position to a second position, and applying force to the plunger of the first syringe barrel and the second syringe barrel in an alternating manner to mix contents of the first syringe barrel and the second syringe barrel.

The Summary of the Invention is neither intended nor should it be construed as being representative of the full extent and scope of the present disclosure. The present disclosure is set forth in various levels of detail in the Summary as well as in the attached drawings and the Detailed Description and no limitation as to the scope of the present disclosure is intended by either the inclusion or non-inclusion of elements, components, etc. in this Summary. Additional aspects of the present disclosure will become more readily apparent from the Detailed Description, particularly when taken together with the drawings.

BRIEF DESCRIPTION OF THE DRAWINGS

Those of skill in the art will recognize that the following description is merely illustrative of the principles of the disclosure, which may be applied in various ways to provide many different alternative embodiments. This description is made for illustrating the general principles of the teachings of this disclosure and is not meant to limit the inventive concepts disclosed herein.

The accompanying drawings, which are incorporated in and constitute a part of the specification, illustrate embodiments of the disclosure and together with the general description of the disclosure given above and the detailed description of the drawings given below, serve to explain the principles of the disclosure.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

Figure 1:
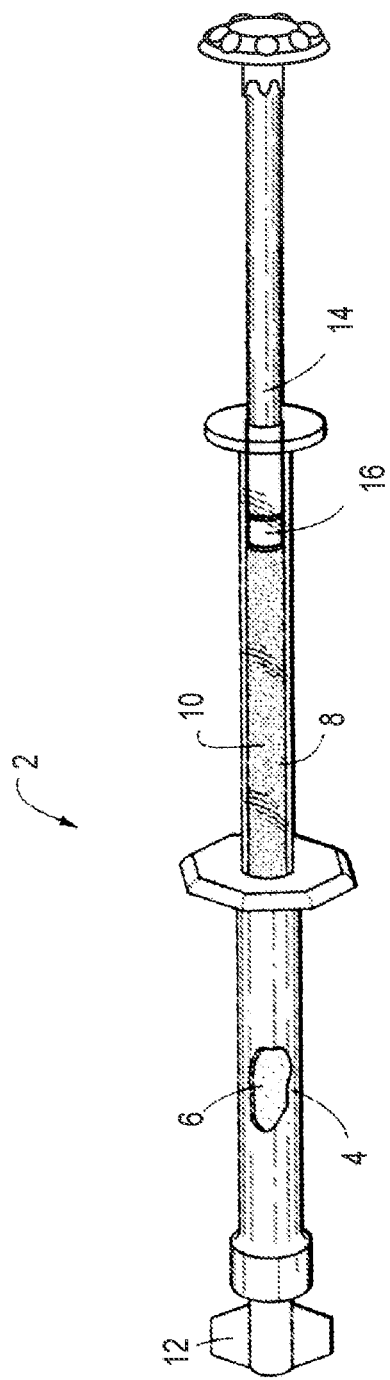

FIG. 1 is a perspective view of a mixing syringe system.

Figure 2:
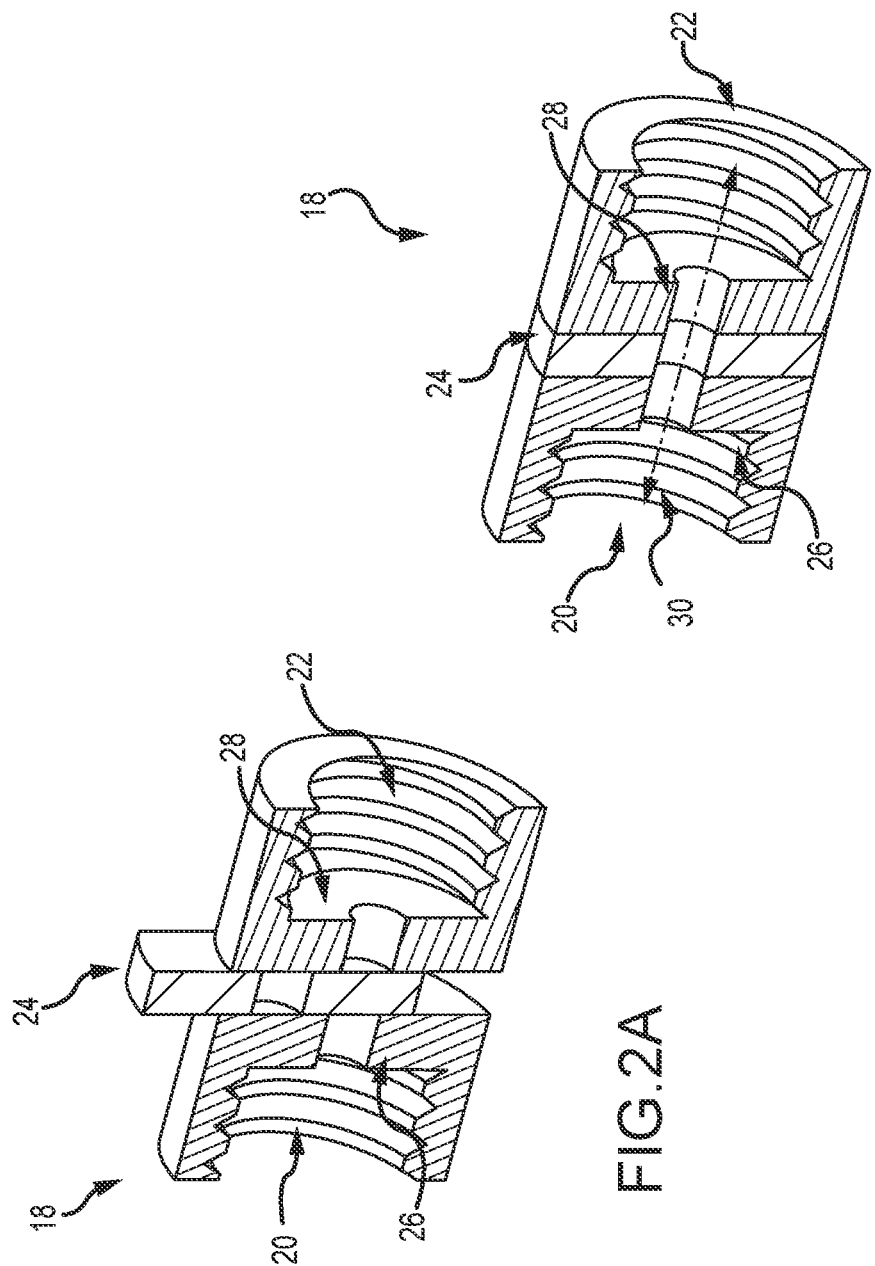

FIG. 2A is a cut-away perspective view of a component of a mixing syringe system according to one embodiment of the present disclosure.

FIG. 2B is a cut-away perspective view of a component of a mixing syringe system according to one embodiment of the present disclosure.

Figure 3:
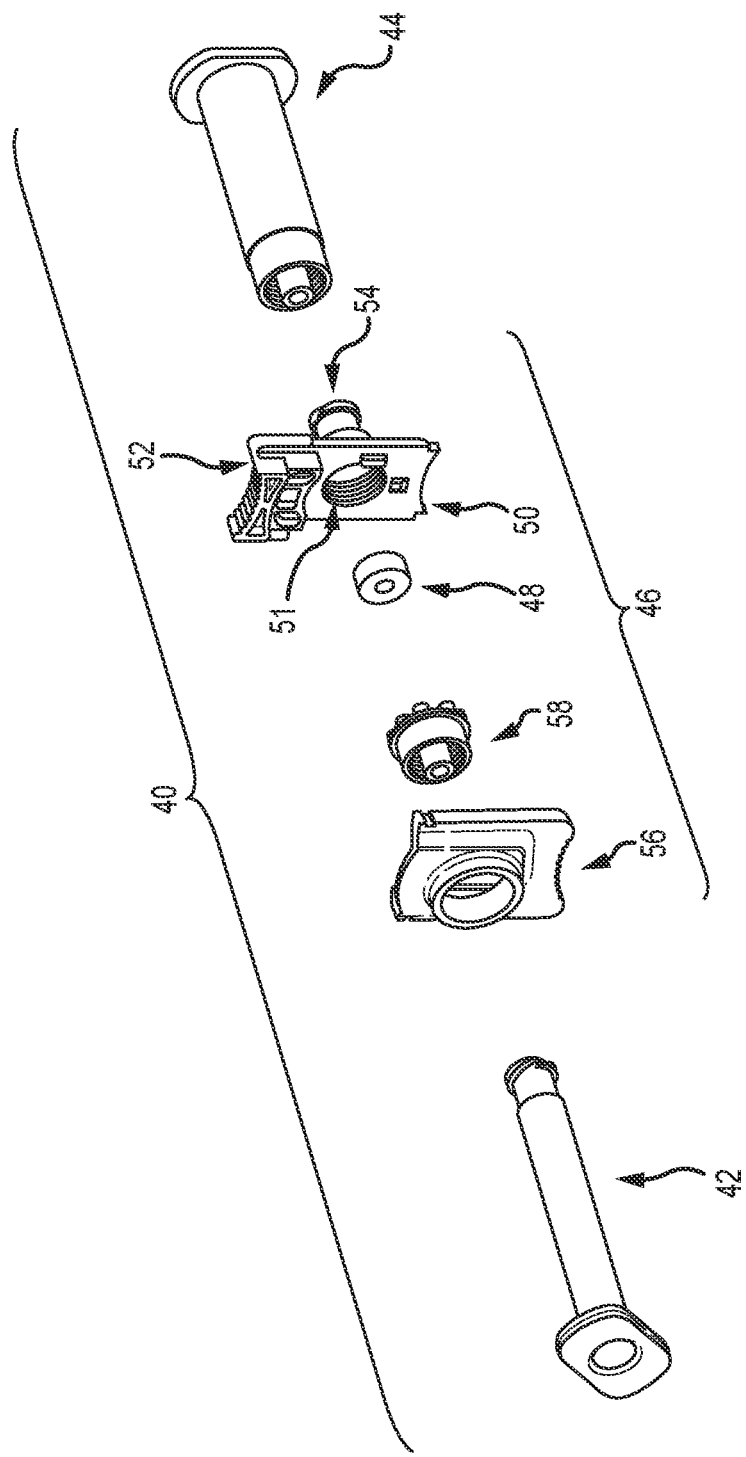

FIG. 3 is an exploded perspective view of a mixing syringe system according to one embodiment of the present disclosure.

FIG. 4A is a perspective view of a component of a mixing syringe system according to one embodiment of the present disclosure.

FIG. 4B is a perspective view of a component of a mixing syringe system according to one embodiment of the present disclosure.

FIG. 4C is a perspective view of a component of a mixing syringe system according to one embodiment of the present disclosure.

Figure 5B:
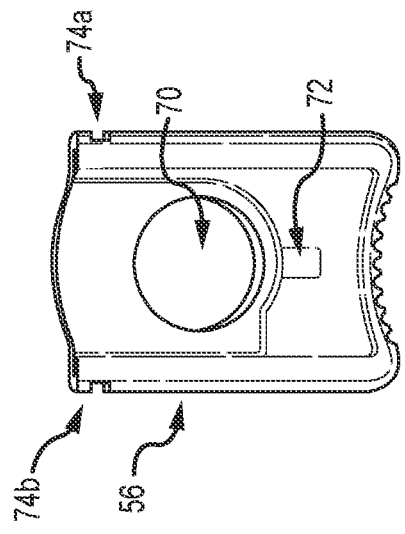
Figure 5D:
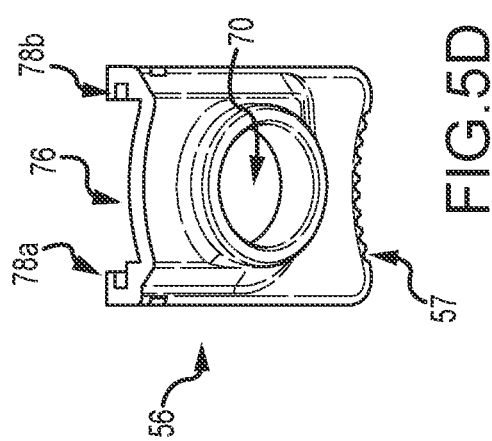
Figure 5A:
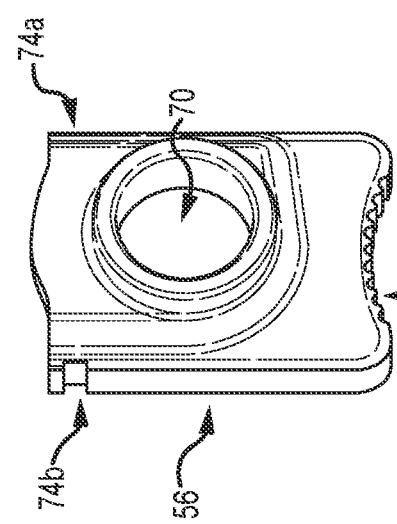

FIG. 5A is a perspective view of a component of a mixing syringe system according to one embodiment of the present disclosure.

FIG. 5B is a perspective view of a component of a mixing syringe system according to one embodiment of the present disclosure.

Figure 5C:
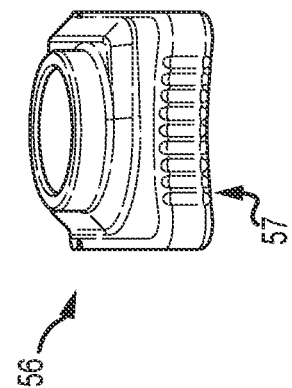

FIG. 5C is a perspective view of a component of a mixing syringe system according to one embodiment of the present disclosure.

FIG. 5D is a perspective view of a component of a mixing syringe system according to one embodiment of the present disclosure.

Figure 6B:
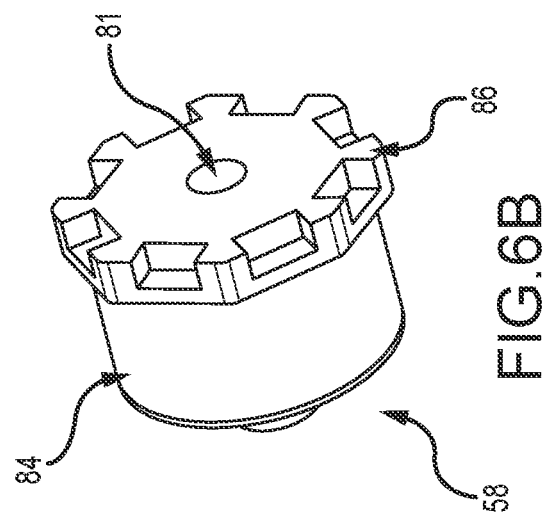
Figure 6A:
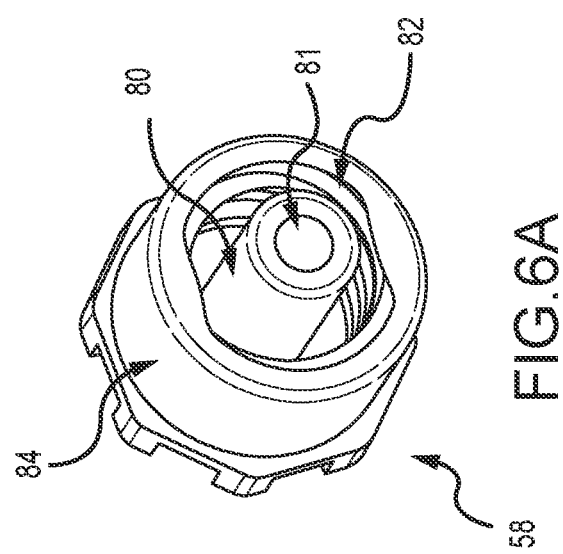

FIG. 6A is a perspective view of a component of a mixing syringe system according to one embodiment of the present disclosure.

FIG. 6B is a perspective view of a component of a mixing syringe system according to one embodiment of the present disclosure.

Figure 7A:
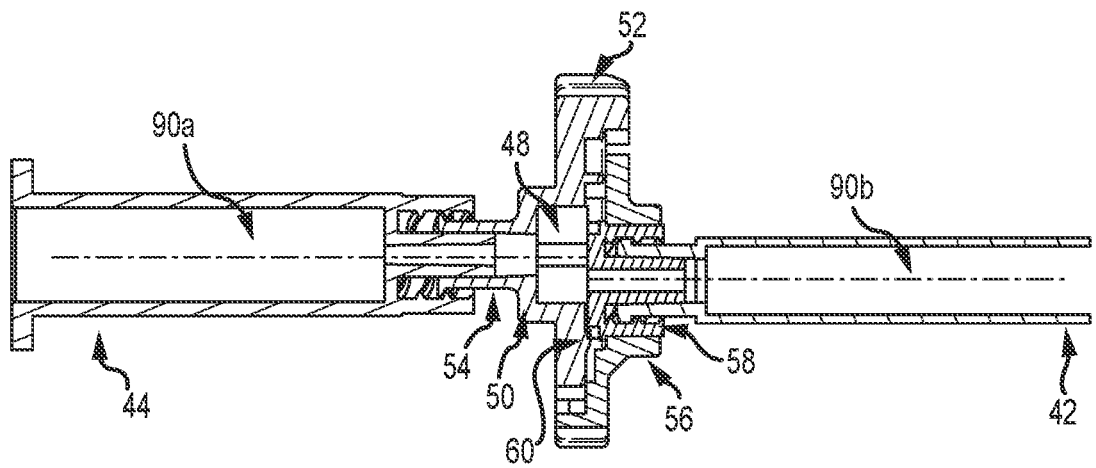

FIG. 7A is a cross-sectional elevation view of a mixing syringe system according to one embodiment of the present disclosure.

Figure 7B:
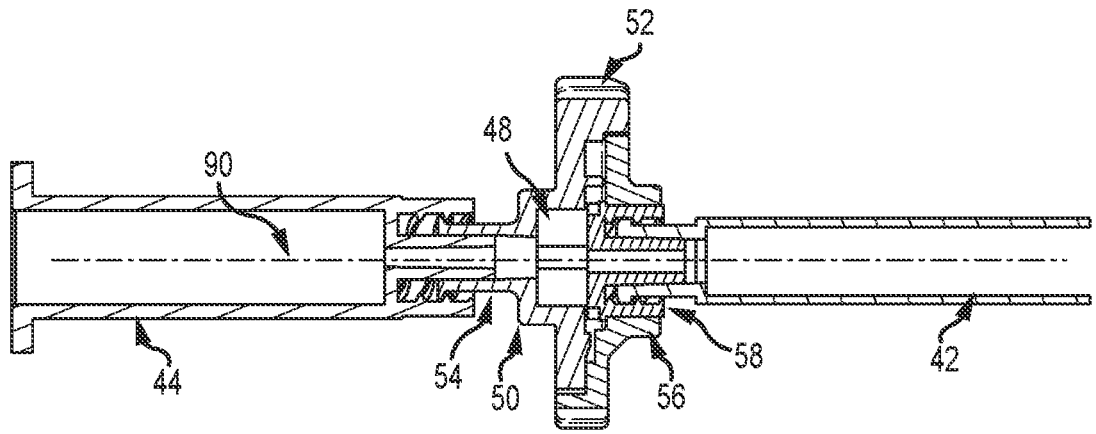

FIG. 7B is a cross-sectional elevation view of a mixing syringe system according to one embodiment of the present disclosure.

Figure 8:
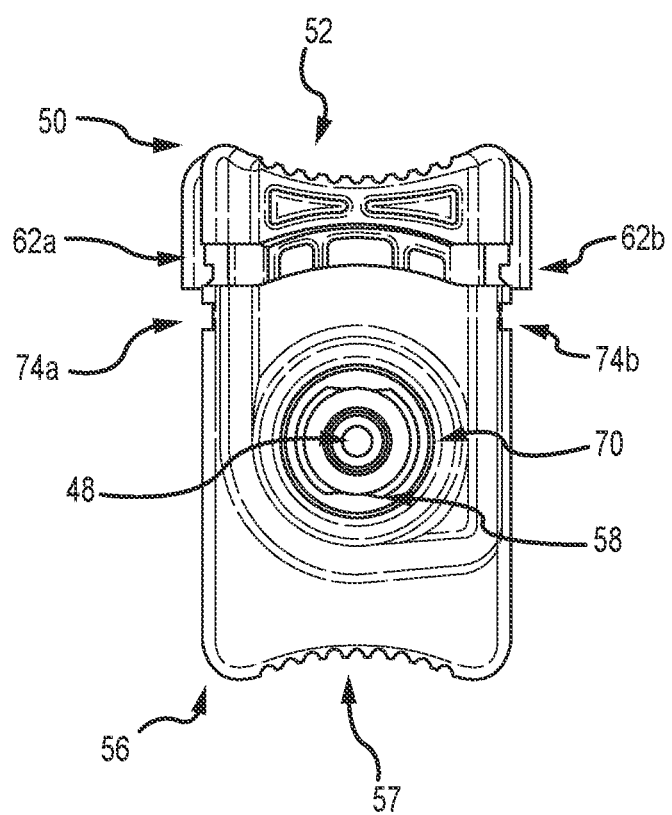

FIG. 8 is an elevation view of components of a mixing syringe system according to an embodiment of the present disclosure.

FIG. 9 is an elevation view of components of a mixing syringe system according to an embodiment of the present disclosure.

FIG. 10 is perspective view of a mixing system and associated packaging according to an embodiment of the present disclosure.

FIG. 11A is a cross-sectional elevation view of a component of a syringe mixing system according to one embodiment of the present disclosure.

FIG. 11B is a cross-sectional elevation view of the component of FIG. 11A in a second position.

Figure 12A:
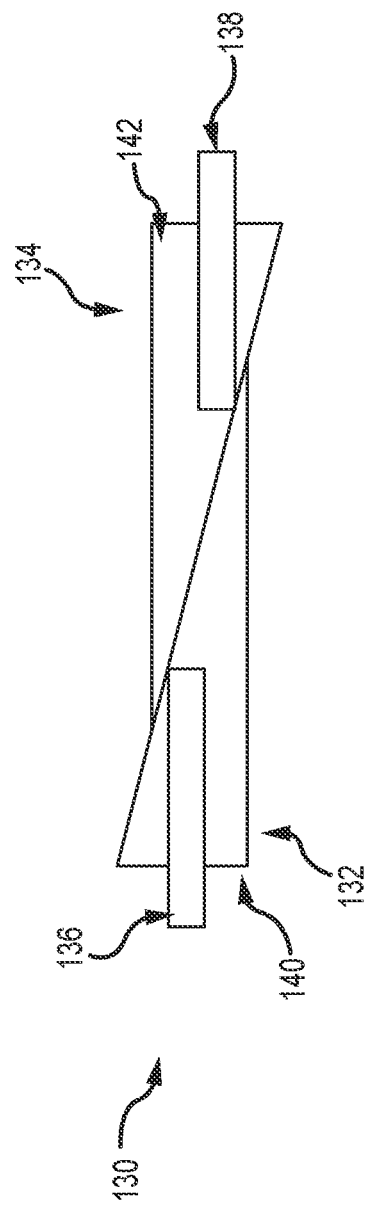

FIG. 12A is a cross-sectional elevation view of a component of a syringe mixing system according to one embodiment of the present disclosure.

Figure 12B:
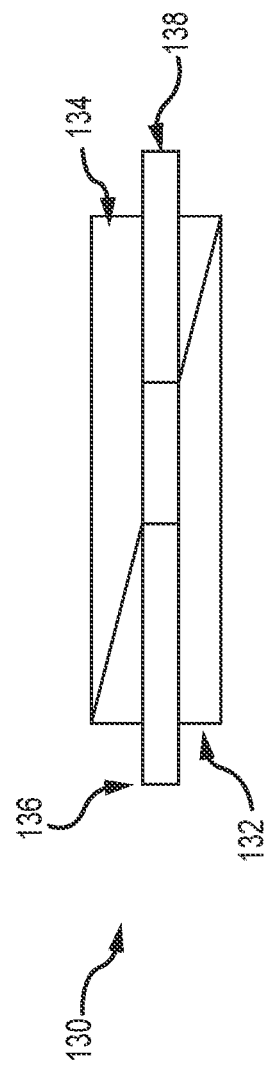

FIG. 12B is a cross-sectional elevation view of the component of FIG. 12A in a second position.

FIG. 12C is a side view of a component of a syringe mixing system according to one embodiment of the present disclosure.

FIG. 12D is a front view of the component of the embodiment of FIG. 12C.

FIG. 12E provides front and side elevation views of the component of the embodiment of FIG. 12C.

FIG. 12F provides front and side elevation views of the component of the embodiment of FIG. 12C.

FIG. 13 is an exploded view of a syringe mixing system according to one embodiment of the present disclosure.

FIG. 14A is a perspective view of a component of a mixing syringe system according to one embodiment of the present disclosure.

FIG. 14B is a perspective view of a component of a mixing syringe system according to one embodiment of the present disclosure.

FIG. 14C is a perspective view of a component of a mixing syringe system according to one embodiment of the present disclosure.

Figure 15B:
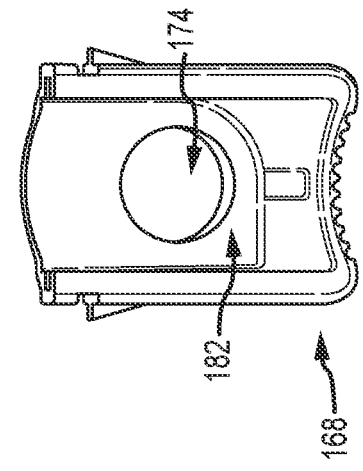
Figure 15D:
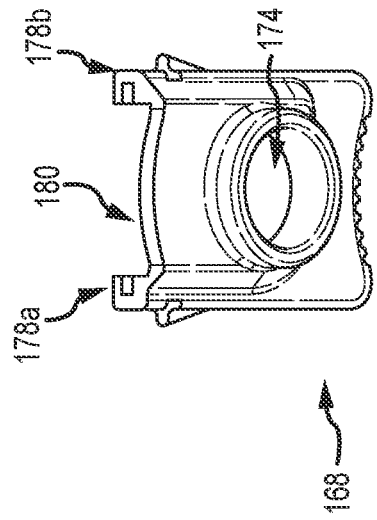
Figure 15A:
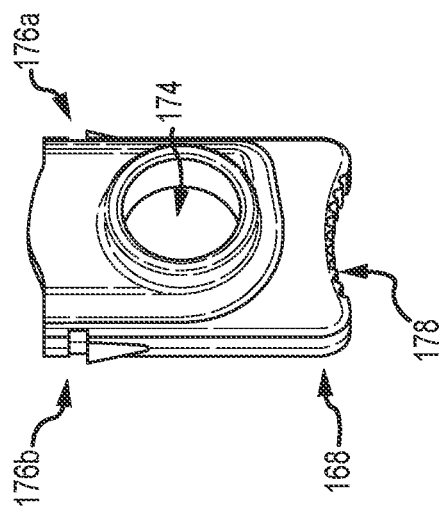

FIG. 15A is a perspective view of a component of a mixing syringe system according to one embodiment of the present disclosure.

FIG. 15B is a perspective view of a component of a mixing syringe system according to one embodiment of the present disclosure.

Figure 15C:
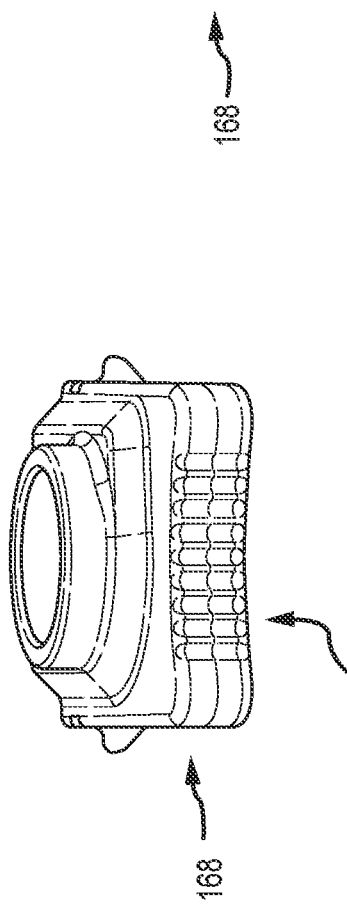

FIG. 15C is a perspective view of a component of a mixing syringe system according to one embodiment of the present disclosure.

FIG. 15D is a perspective view of a component of a mixing syringe system according to one embodiment of the present disclosure.

Figure 16B:
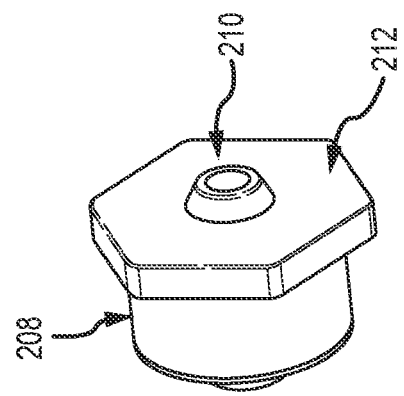
Figure 16A:
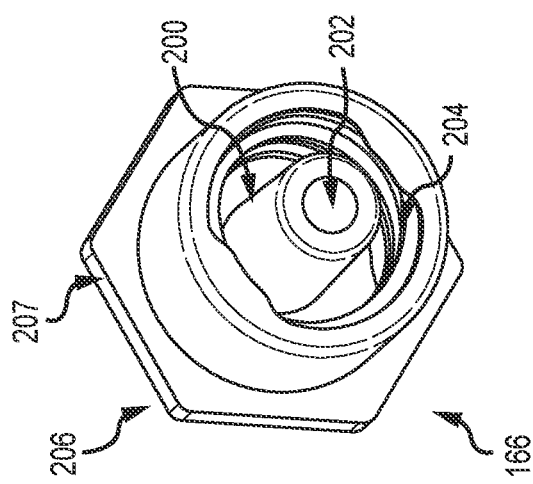

FIG. 16A is a perspective view of a component of a mixing syringe system according to one embodiment of the present disclosure.

FIG. 16B is a perspective view of a component of a mixing syringe system according to one embodiment of the present disclosure.

Figure 17A:
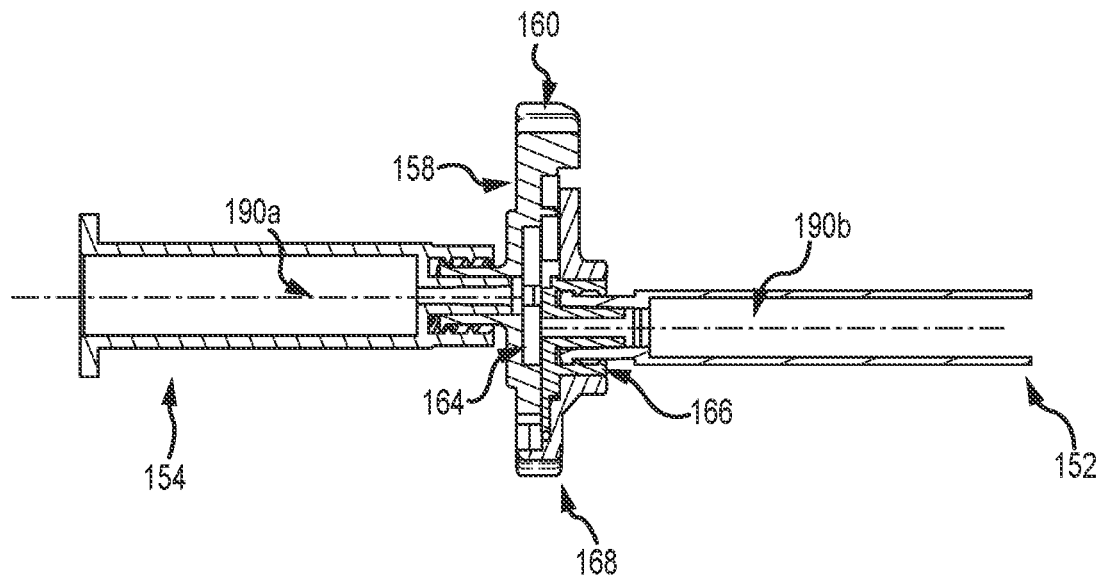

FIG. 17A is a cross-sectional elevation view of a mixing syringe system according to one embodiment of the present disclosure.

Figure 17B:
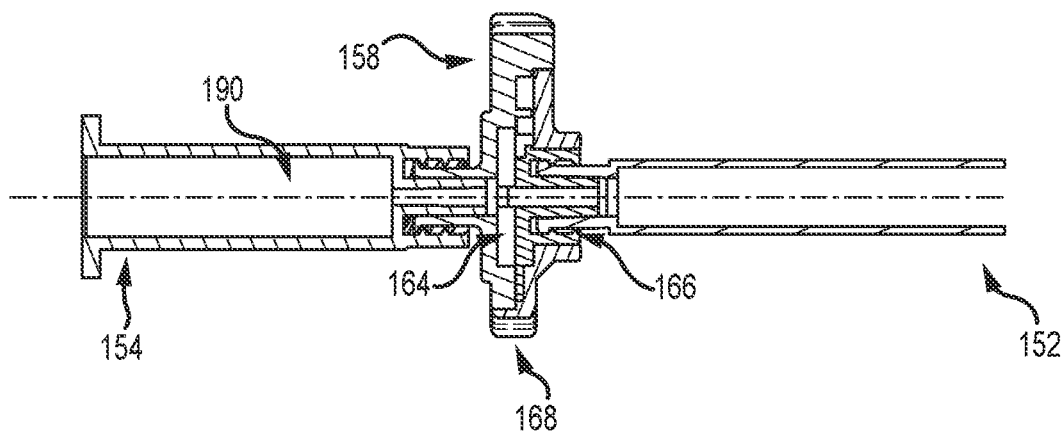

FIG. 17B is a cross-sectional elevation view of a mixing syringe system according to one embodiment of the present disclosure.

DETAILED DESCRIPTION

FIG. 1 is a perspective view of a known syringe-to-syringe mixing system. As shown, the system 2 comprises a first syringe 4 housing contents 6 and a second syringe 8 housing contents 10. The syringes 4, 8 are connected at their respective distal dispensing ends. Fluid and materials housed within the syringes may be moved from one syringe to another and mixing can occur by applying forces to the syringe plunger rods 12, 14. At least one plunger 16 is operable to force contents between the syringes 4, 8 and produce a mixing action. Various known syringes and systems require the first syringe and second syringe to be directly connected (e.g. threaded together) by a user just prior to mixing and administration. The syringes are then disconnected with one syringe comprising a mixed solution for administration.

FIGS. 2A-2B are perspective view of a component of a valve assembly for a mixing system contemplated for use with syringes according to one embodiment of the present disclosure. As shown, a coupling element is provided as a syringe coupler 18. The syringe coupler 18 comprises a device that is operable to receive a first and second syringe and selectively provide the syringes in fluid communication with one another. The syringe coupler 18 comprises a first end 20 operable to receive a first syringe and a second end 22 operable to receive a second syringe. The syringes (not shown in FIGS. 2A-2B) are contemplated as comprising distal ends with open outlets for dispensing and/or receiving materials. FIGS. 2A-2B illustrate the first and second ends 20, 22 as comprising female threaded connection members. It will be recognized, however, that syringe couplers of the present disclosure are not limited to threaded connections and one or both of the first and second ends may comprise alternative structure for receiving and securing syringes. As further shown in FIGS. 2A-2B, the syringe coupler 18 comprise a valve element comprising a displaceable member 24 that is moveable relative to the coupler 18. First and second internal members 26, 28 are provided that each comprise an aperture and which cooperate with the displaceable member.

As shown in FIG. 2A, a closed position is provided wherein the displaceable member 24 is in a first position and a central aperture of the displaceable member is offset from the apertures of the first and second internal members 26, 28. In this position, fluid and gaseous vapor flow is at least partially and preferably fully occluded through the coupler. Accordingly, syringes connected to the coupler 18 cannot exchange materials in the closed position. The displaceable member 24 is offset and preferably comprises a surface or user-interface that is accessible to a user and operable to receive an activation force.

An activation force upon the displaceable member 24 is operable to move the displaceable member from a first position (FIG. 2A) wherein fluid flow through the member 18 is occluded to a second position (FIG. 2B) wherein an aperture of the displaceable member 24 is aligned with apertures of the internal members 26, 28 and a fluid flow path 30 is formed through the device. As shown and described the syringe coupler 18 provides means for securing at least one and preferably two syringes, and comprises a valve element to selectively allow for transmission of materials between syringes upon activation of the valve element by a user.

FIG. 3 is an exploded perspective view of a mixing syringe system 40 according to another embodiment of the present disclosure. As shown, the system 40 comprises a first syringe 42 and a second syringe 44. The first and second syringes are contemplated as initially comprising solid or liquid contents. For example, the first syringe 42 may house or comprise a polymer-solvent system such as, but not limited to, a biodegradable polymer dissolved in NMP and the second syringe 44 may comprise a drug lyophilizate such as, but not limited to, lyophilized leuprolide acetate. Although the discussion of various embodiments of the present disclosure contemplates and refers to the first syringe comprising NMP and the second syringe comprising a drug lyophilizate, it will be recognized that the disclosure is not limited to that arrangement. Syringe contents may be altered, rearranged and substituted while remaining within the scope of the inventions of the present disclosure. Indeed, inventive aspects of the present disclosure are believed to reside in features and components of the described system regardless of which materials (or if any materials) are provided within the components.

Unwanted NMP migration (i.e. unintended migration prior to mixing) has been recognized as providing various complications including, for example, degrading or destroying shelf-life of contents. It is an object of various embodiments of the present disclosure to reduce or eliminate the risks of unwanted NMP migration while storing NMP and a drug lyophilizate in close proximity prior to mixing.

The contents of the first and second syringes 42, 44 may be mixed to formulate a solution or suspension for administration as shown and described herein. The embodiment of FIG. 3 comprises a syringe coupler 46. The syringe coupler 46 of the depicted embodiment is operable to receive and connect to the first and second syringes 42, 44, selectively prevent and enable fluid transfer between the two syringes, and selectively prevent removal of at least one syringe.

Each syringe 42, 44 comprises a barrel having an internal volume, proximal ends for receiving a plunger rod (not shown in FIG. 3), and distal ends with dispensing outlets wherein the distal ends are operable to connect to the syringe coupler 46. The syringe coupler 46 comprises a valve assembly with a sealing element 48 that nests within recessed area 51 of a displaceable member 50. In some embodiments, including that shown in FIG. 3, the sealing element comprises an annular sealing element. The displaceable member comprises a user-interface 52 that is operable to be contacted by and receive a force from a user and a male extension 54 for receiving the second syringe 44. The syringe coupler 46 further comprises a guide member 56 within which the displaceable member is provided. The guide member comprises a user-interface 57 (FIG. 5A) that is operable to be contacted by and receive a force from a user. A rotatable Luer lock member 58 is provided. The rotatable Luer lock member 58 of the depicted embodiment comprises a proximal end with a male fitting operable to connect to the first syringe 42, and a distal end comprising a cog with teeth or projections for selectively limiting rotation of the rotatable Luer lock member 58 prior to activation.

FIGS. 4A-4C are perspective views showing the displaceable member 50 in greater detail. As shown, the displaceable member 50 comprises a user-interface 52 operable to be acted upon by a user. In preferred embodiments, the displaceable member is displaceable in a downward direction (at least relative to FIG. 4A) and is preferably not operable to return to an initial or first position. A male extension 54 is provided on one side of the member for receiving a syringe. A recess 56 is provided on an opposing side of the displaceable member relative to the male extension 54. The recess 56 is operable to receive a sealing element, such as the annular sealing element 48 of FIG. 3. A channel is provided through the displaceable member 50, wherein the channel extends through the male extension 54 and into the recess 56. Preferably, a sealing element comprises an aperture that is aligned with the channel of the displaceable member 50.

As shown in FIGS. 4A-4B, first and second projections 60, 75 are provided on the displaceable member 50. The projections 60, 75 are displaceable with the member 50 and are moveable relative to at least the rotatable Luer lock member 58 of an assembled device. In a first position, at least one of the projections is provided in contact with the rotatable Luer lock member 58 to prevent rotation of the member 58. This contact and related locking of the rotatable Luer lock member 58 enables a first syringe to be threaded onto (and threadably removed from) the rotatable Luer lock member 58 prior to activation of the assembled device. Movement of the displaceable member 50 by user activation results in displacing the projections 60, 75 such that they are not in contact with the Luer lock member 58. With rotation of the rotatable Luer lock member enabled, the member 58 is free to spin within the displaceable member 50. Without resistance, a syringe connected to the rotatable Luer lock member 58 is prevented from being threadably detached from the syringe coupler even if and when a rotation is applied in an attempt to remove the syringe. It is an object of the present disclosure to provide a syringe coupler 46 that retains at least one syringe such that a user is prevented from using the first syringe for administration and is thereby only given the option of administering the mixed contents with the second syringe.

As shown in FIGS. 4A-4C, the displaceable member 50 also comprises clips or resilient projections 62a, 62b. The resilient projections 62a, 62b are operable to flex outwardly and do not substantially impede a downward movement of the displaceable member 50. When provided in a second position, however, the resilient projections 62a, 62b are secured to the guide member 56 at least in part due to an inherent restoring force of the projections. The resilient projections 62a, 62b secure the displaceable member 50 in a second position within guide member 56 through engagement of said resilient projections 62a, 62b into recesses 74a, 74b located upon guide member 56 to prevent or inhibit the displaceable member from being returned to a first position.

FIGS. 5A-5D are perspective views of a guide member 56 according to one embodiment and contemplated for use and cooperation with the displaceable member 50 is FIGS. 4A-4C. As shown, the guide member 56 comprises a central aperture 70 to permit fluid flow and to receive a rotatable Luer lock member 58 of embodiments of the disclosure. The guide member 56 is provided to slidably receive at least a portion of a displaceable member 50. As shown, the guide member 56 comprises a receiving portion 76 with first and second slot members 78a, 78b to receive a displaceable member 50. The guide member comprises a user-interface 57 that is operable to be contacted by and receive a force from a user. In certain embodiments, and as shown in FIGS. 5A-5D, the user-interface 57 is contemplated as comprising a gripping or contact surface having ridges to reduce slipping and provide ergonomic benefits.

A surface of the guide member 56 comprises a channel 72 (FIG. 5B) to receive and guide the movement of a ramp-like projection 60 of the displaceable member 50 (FIG. 4B, for example). During assembly of the syringe device connector, the guide member 56 operably receives the displaceable member 50 such that projection 60 of the displaceable member 50 contacts an upper surface of receiving portion 76 of the guide member 56 (at least relative to the direction in FIG. 5B) to induce a physical separation between the surface of the displaceable member 50 and the receiving portion 76 of the guide member 76. The ramp-like projection 60 allows a distal surface of the annular sealing element 48 nesting within recessed area 51 of the displaceable member 50 to slide over the distal surface of Luer lock member 58 nested within the central aperture 70 of guide member 56. Once ramp-like projection 60 traverses the distal surface of Luer lock member 58 nested within the central aperture 70 of guide member 56, the projection 60 is operably received into one of the plurality of teeth 86 of the Luer lock member 58. Operable engagement of ramp-like projection 60 into one of the plurality of teeth 86 of the Luer lock member 58 collapses the physical separation induced during crossing of the distal surface of Luer lock member 58 such that the distal surface of the annular sealing element 48 nested within recessed area 51 of the displaceable member 50 is brought into direct contact with the distal surface of Luer lock member 58 within the central aperture 70 of guide member 56 causing the annular sealing element 48 to compress. Once ramp-like projection 60 is operably received into one of the plurality of teeth 86 of the Luer lock member 58 and annular sealing element 48 is compressed, the assembled syringe device connector is configured into the first position prior to activation. The ramp-like projection 60 is operable to allow the guide member 56 to translate over various irregular surface including, for example, a central aperture of the Luer lock member 58.

In a first position prior to activation, the ramp-like projection 60 and the projection of the displaceable member 50 are provided in communication with a rotatable Luer lock member 58 to prevent rotation thereof. In a second position subsequent to activation, the projection 60 of the displaceable member 50 is displaced into the channel 72 of guide member 56 while projection 75 of the displaceable member is displaced into the recessed area 73 (FIG. 9) on the guide member 56 where the projections 60, 75 assume positions that do not contact or impede rotation of the rotatable Luer lock member 58. The second position further comprises a position wherein a fluid flow channel is created. Specifically, an annular sealing element 48 provided within the displaceable member 50 is moved from a first position characterized by a channel of the annular sealing element 48 being offset from and preventing flow between inlets and outlets of interconnected syringes and a second position characterized by the channel of the annular sealing element 48 being provided in axial alignment with the syringe outlets and inlets.

As shown in FIGS. 5A-5B, for example, the guide member 56 further comprises recesses 74a, 74b that are operable to receive resilient projections 62a, 62b of a displaceable member and secure the syringe coupler in a second position. The recesses 74a, 74b are operable to prevent or at least impede a user from returning the device to a first position after activation of the syringe coupler.

FIGS. 6A-6B are perspective views of a rotatable Luer lock member 58 according to one embodiment of the present disclosure. As shown, the rotatable Luer lock member 58 comprises a first end with a male Luer lock 80 that provides a means of attachment to a first syringe as well as a fluid flow path through a central aperture 81 of the member 58. The male Luer lock 80 is at least partially provided within a threaded female member 82 that is operable to threadingly engage a first syringe. A bearing surface 84 is provided on an exterior of the member 58. The bearing surface 84 is operable to be provided in the central aperture 70 of the guide member 56 and contact the guide member. The bearing surface 84 of the rotatable Luer lock member 58 comprises a surface upon which the member 58 can rotate (when unlocked) and contact the central aperture 70 of guide member 56. The rotatable Luer lock member 58 further comprises a plurality of teeth 86 operable to act as locking members and selectively prevent rotation of the rotatable Luer lock member 58. Specifically, when a projection of the present disclosure (75 of FIG. 4B, for example) is provided in a first position, the projection 75 is provided in contact with at least one of the plurality of teeth 86 such that rotation of the rotatable Luer lock member 58 (at least with respect to the guide member 56 and the displaceable member 50) is prevented. The secured nature or state of the member 58 in the first position allows a user to thread a first syringe within the threaded female member 82. When the displaceable member is displaced as shown and described herein, the projection 75 is moved away from the plurality of teeth 86 of the rotatable Luer lock member 58 such that rotation is unopposed and the member 58 is allowed to rotate relative to the guide member 56 and the displaceable member. This freedom of rotation prevents or at least inhibits the un-threading and removal of the first syringe as a rotation force applied to the syringe will cause a rotation of the rotatable Luer lock member 58. With no significant oppositional force on the rotatable Luer lock member 58 or threaded female member 82, un-threading will not occur and the first syringe is effectively prevented from being removed from the syringe coupler.

FIGS. 7A-7B are cross-sectional elevation views of a system according to an embodiment of the present disclosure. As shown and previously described, the system comprises a first syringe 42 and a second syringe 44. The syringes 42, 44 are connected to a syringe coupler comprising a displaceable member 50 with a user-interface 52, an annular sealing element 48, a guide member 56, and a rotatable Luer lock member 58 provided at least partially within the guide member 56. The system is shown as being provided in a first position in FIG. 7A. The first position comprises a position wherein the displaceable member and associated annular sealing element 48 are provided offset from a central axis and passageway of the rotatable Luer lock member 58. Specifically a fluid flow path 90a of the second syringe 44, the male extension 54 of the displaceable member 50, and the sealing member 48 is offset from and not in communication with a fluid flow path 90b of the first syringe 42 and the rotatable Luer lock member 58. Fluid and gaseous vapor flow between syringes 42, 44 is thus prevented.

FIG. 7B depicts the system in a second position wherein the displaceable member has been displaced by application of force upon the user-interface 52 (for example). As shown, fluid pathway 90a of FIG. 7A and related components have been displaced such that a continuous fluid pathway 90 is provided and fluid flow between the first syringe 42 and second syringe 44 is enabled. Mixing of contents is thus enabled, wherein plunger rods (not shown in FIGS. 7A-7B) associated with the first and second syringes 42, 44 are operable to force contents between the syringes.

Systems, devices and methods of the present disclosure are not limited to any particular therapeutic agent(s), solution(s), suspension(s), gas, or a combination thereof. In some embodiments, for example, it is contemplated that that one or more non-lyophilized materials are provided in syringes of the present disclosure. In some embodiments, a gas (e.g. Cobalt gas) is provided in a syringe for mixing with contents of a second syringe. Such embodiments, including others, complete that mixing syringe systems of the present disclosure comprise gas-impermeable materials to prevent gas permeation and migration. However, in certain preferred embodiments, a first syringe 42 is initially provided with a liquid formulation component such as a polymer-solvent system and a second syringe is provided with an API, which may, in some non-limiting instances, be present as a lyophilized power. In such embodiments, the contents are stored separately with each respective syringe which are interconnected to the syringe coupler with the displaceable member provided in the first position (FIG. 7A). To administer a therapeutic agent, the displaceable member is depressed or otherwise activated, creating the fluid-flow pathway 90 of FIG. 7B. Repetitive mixing may then be performed by forcing the polymer-solvent of the first syringe 42 into the second syringe that comprises the API, forcing the contents back to the first syringe, and repeating the process until desired mixing is achieved. As discussed, the second position of FIG. 7B is characterized by the presence of a fluid flow path between the two syringes 42, 44, as well as by the disengagement of the displaceable member 50 and the rotatable Luer lock member 58. Specifically, the second position (FIG. 7B) comprises a position in which the rotatable Luer lock member 58 is free to rotate within the syringe coupler and the first syringe 42 is prevented from unthreading or detachment. Accordingly, the second syringe 44 preferably comprising the mixed or prepared agent is detachable for use as an injection syringe while the first syringe is inoperable for such purposes.

FIG. 8 is an elevation view of components of a syringe coupler according to an embodiment of the present disclosure. As shown, a displaceable member 50 and a guide member 56 are provided in a first position. The first position is suitable for shipping and storage wherein fluid and gas vapor flow between interconnected syringes is fully or at least partially occluded. The displaceable member 50 comprises an interconnected sealing element 48. The sealing element 48 comprises a central aperture, but the central aperture is offset from the fluid flow path of the guide member 56 and rotatable Luer lock member 58 such that fluid flow through the device is occluded. The displaceable member 50 and the guide member 56 comprise user-interface portions 52, 57, respectively. Force may be applied to one or more of the user-interfaces 52, 57 to convert the device from the first position to a second position wherein the displaceable member 50 is displaced relative to the guide member and a fluid flow path is created (FIG. 7B, for example).

The displaceable member 50 comprises first and second projections 62a, 62b that are operable to be outwardly displaced upon downward movement of the displaceable member. The first and second projections 62a, 62b are secured within the recesses 74a, 74b of the guide member 56 and move inwardly based on their inherent material properties and elasticity. The placement of the first and second projections 62a, 62b within or partially within the recesses 74a, 74b of the guide member 56 prevent or inhibit a return movement of the displaceable member 50 back to the first position.

FIG. 9 is an elevation view of cooperating surfaces of a displaceable member 50 and a guide member 56. As shown, the displaceable member 50 comprises a ramp-like projection 60 that is operable to guide installation and interconnection of the displaceable member 50 and the guide member 56. A channel 72 is provided to receive and house the projection 60. In a first position, rotation of a rotatable Luer locking member is substantially impeded by a second projection 75 being provided in contact with a portion of the Luer locking member. In a second position, the second projection 75 is displaced downwardly (at least with respect to FIG. 9) and the rotatable Luer locking member can freely rotate within the aperture 70 of the guide member 56. The second projection 75 is provided on the displaceable member 50 and is operable to contact at least one of a plurality of teeth of a rotatable Luer lock member 58 (not shown) in a first position and which is disposed into slot 73 provided on the guide member 56 in a second position. In addition to locking and unlocking a rotatable Luer lock member 58 (not shown), the projection 75 of the displaceable member and the corresponding features of the guide member 56 serve to limit displacement of the displaceable member and ensure that the displaceable member comes to rest in a second position wherein a fluid flow path is aligned.

FIG. 10 is a perspective view of a syringe-to-syringe mixing system provided in packaging tray 100 according to one embodiment of the present disclosure. As shown, the system comprises a first and second syringe 42, 44 joined by a syringe coupler 46 including (for example) those shown and described herein. The syringes 42, 44 are connected to the syringe coupler 46 for and during shipping and storage in a packaging member 100. The packaging member 100 of FIG. 10 comprises a clamshell device rotatable about a hinge 104 and in which the system is stored. Contours and indentations 102 of the packaging member 100 are contemplated as being provided to restrict movement of certain components of the system including, for example, unwanted movement of a displaceable member (50 in FIG. 3, for example) and/or unwanted movement of syringe plunger rods. While various embodiments of the present disclosure contemplate the provision of first and second syringes attached to a syringe coupler for shipping and wherein the system is provided to an end user in an assembled or interconnected state, alternative embodiments contemplate the provision of one or more syringes initially detached from a syringe coupler. In such embodiments, a user such as a healthcare professional assembles the devices by connecting one or more syringes to the syringe coupler just prior to conducting mixing operations.

FIG. 11A is a cross-sectional elevation view of a mixing syringe component 110 according to one embodiment of the present disclosure. As shown, the component 110 comprises a valve element that is convertible between a first position (FIG. 11A) and a second position (FIG. 11B). As shown, the component 110 comprises first 112 and second 114 translatable components. The first and second translatable components 112, 114 are operable to be displaced relative to one another from a first position (FIG. 11A) wherein a conduit 116 of the first component 112 is unaligned with a conduit 118 of the second component 114. In the first position, the conduits 116, 118 are not connected and fluid flow between the components is substantially occluded. The first component 112 and second component 114 are displaceable to a second position (FIG. 11B) wherein the conduits 116, 118 have been brought into connection and/or aligned such that fluid flow between the components 112, 114 is enabled.

In certain embodiments, proximal ends 120, 122 of the components are operable to receive a syringe. An axial compression force on the syringe(s) (not shown in FIGS. 11A-11B) is operable to displace the components from the misaligned position of FIG. 11A to the aligned position of FIG. 11B in which fluid is allowed to pass between the components and related syringes. Although not shown in FIGS. 11A-11B, the proximal ends 120, 122 of the components are contemplated as comprising securing means for syringes. Securing means are contemplated as comprising, for example, threaded connection members, Luer lock components, and similar features to selectively secure a syringe to the components. In operation, a user may apply a compressive force to one or more syringes connected to the mixing syringe component 110 of FIGS. 11A-11B to displace the device from the position of FIG. 11A to the mixing position of FIG. 11B. The user may then proceed with mixing operations by sequentially applying a force to plunger rods of interconnected syringes as shown and described herein. The arrangement of the device of FIGS. 11A-11B therefore reduces process steps and reduces the need for a user to reposition their hands between activation of the valve element and a mixing operation.

It is further contemplated that the embodiments of FIGS. 11A-11B comprise stops or limiting members to prevent movement of the components beyond a desired position wherein mixing is enabled. The limiting members may further comprise resilient stops or connection members to secure the devices in a mixing position and prevent reverse translation.

FIG. 12A is a cross-sectional elevation view of a mixing syringe component 130 according to one embodiment of the present disclosure. As shown, the component 130 comprises a valve element that is convertible between a first position (FIG. 12A) and a second position (FIG. 12B). As shown, the component 130 comprises first 132 and second 134 translatable components. The first and second translatable components 132, 134 are operable to be displaced relative to one another from a first position (FIG. 12A) wherein a conduit 136 of the first component 132 is unaligned with a conduit 138 of the second component 134. In the first position, the conduits 136, 138 are not connected and fluid flow between the components is substantially occluded. The first component 132 and second component 132 are displaceable to a second position (FIG. 12B) wherein the components 132, 134 provide a ramped or cammed surface, and wherein the conduits 132, 134 have been brought into connection and/or aligned such that fluid flow between the components 132, 134 is enabled.

In certain embodiments, proximal ends 140, 142 of the components are operable to receive a syringe. An axial compression force on the syringe(s) (not shown in FIGS. 12A-121B) is operable to displace the components from the misaligned position of FIG. 12A to the aligned position of FIG. 12B in which fluid is allowed to pass between the components and related syringes. Although not shown in FIGS. 12A-12B, the proximal ends 140, 142 of the components are contemplated as comprising securing means for syringes. Securing means are contemplated as comprising, for example, threaded connection members, Luer lock components, and similar features to selectively secure a syringe to the components. In operation, a user may apply a compressive force to one or more syringes connected to the mixing syringe component 130 of FIGS. 12A-12B to displace the device from the position of FIG. 12A to the mixing position of FIG. 12B. The user may then proceed with mixing operations by sequentially applying a force to plunger rods of interconnected syringes as shown and described herein. The arrangement of the device of FIGS. 12A-12B therefore reduces process steps and reduces the need for a user to reposition their hands between activation of the valve element and a mixing operation.

It is further contemplated that the embodiments of FIGS. 12A-12B comprise stops or limiting members to prevent movement of the components beyond a desired position wherein mixing is enabled. The limiting members may further comprise resilient stops or connection members to secure the devices in a mixing position and prevent reverse translation.

FIG. 12C illustrates a mixing syringe component 300 operable to selectively permit and restrict a fluid flow through the device and associated features. As shown, the component 300 comprises a valve element having a first portion 302 and a second portion 304. Each of the first portion and the second portion comprise an aperture or flow port 306a, 306b. When the flow ports 306a, 306b are offset or misaligned by a certain degree, flow through the component 300 is prevent. The first portion 302 and second portion 304 are rotatable at least relative to one another. Specifically, the portions 302, 304 are rotatable around an axis 308. A pin or axle member is contemplated as being provided to secure the portions and enable rotation. FIG. 12C depicts the first portion 302 and the second portion 304 in disassembled and assembled states.

FIG. 12D is an elevation view of the component 300 of FIG. 12C. The first portion 302 and the second portion 304 are rotationally offset to illustrate a motion and freedom of movement of the device 300. A rotational movement R is operable to place the first portion 302 and the second portion 304 in alignment and selectively enable fluid flow.

FIG. 12E shows the component 300 in a closed position wherein fluid flow is prevented or occluded. As shown, the second portion 304 is rotated relative to the first portion 302 such that the fluid flow ports 306a, 306b are offset and fluid cannot pass through the device 300. The position shown in FIG. 12E is contemplated as being an initial position wherein mixing and fluid flow are prevented.

FIG. 12F shows the component 300 in an aligned position wherein fluid flow is enabled. As shown, the first portion 302 and the second portion 304 have been rotated into alignment wherein the flow ports 306a, 306b are axially aligned and a flow path 312 is created through the component 300.

FIGS. 12C-12F contemplate and depict a device with portions that are rectilinear cubes. It will be recognized, however, that various alternative arrangements are contemplated. For example, the first and second portions shown in FIGS. 12C-12F are also contemplated as being provided as disc-shaped features and/or various other geometric shapes. Additionally, although not shown in FIGS. 12C-12F, one or more stops or détentes are contemplated as being provided to guide or limit an amount of relative rotation between the first portion and the second portion. For example, one or more stops are contemplated as being provided to secured or lock the device in the open position (FIG. 12F, for example). Additionally, a ramp or resistance member is contemplated wherein an initial resistance force is provided that must be overcome in order to open the device and prevent or reduce the risk of accidental activation.

Although not shown in FIGS. 12C-12F, various extensions or user-interface portions are contemplated. For example, the features shown in FIG. 12C-12F may be provided internal to or partially internal to a larger device, and an extension or trigger is provided to enable to control rotation of at least a portion of the component 300.

FIG. 13 is an exploded perspective view of a mixing syringe system 150 according to another embodiment of the present disclosure. As shown, the system 150 comprises a first syringe 152 and a second syringe 154. The first and second syringes are contemplated as initially comprising solid or liquid contents. For example, the first syringe 152 may house or comprise a polymer-solvent system such as, but not limited to, a biodegradable polymer dissolved in NMP and the second syringe 154 may comprise lyophilizate such as, but not limited to, lyophilized leuprolide acetate. Unwanted NMP migration (i.e. unintended migration prior to mixing) has been recognized as providing various complications including, for example, degrading or destroying shelf-life of contents. It is an object of various embodiments of the present disclosure to reduce or eliminate the risks of unwanted NMP migration while storing NMP and a drug lyophilizate in close proximity prior to mixing.

The contents of the first and second syringes 152, 154 may be mixed to formulate a solution or suspension for administration as shown and described herein. The embodiment of FIG. 13 comprises a syringe coupler 156. The syringe coupler 156 of the depicted embodiment is operable to receive and connect to the first and second syringes 152, 154, selectively prevent and enable fluid transfer between the two syringes, and selectively prevent removal of at least one syringe.

Each syringe 152, 154 comprises a barrel having an internal volume, proximal ends for receiving a plunger rod (not shown in FIG. 13), and distal ends with dispensing outlets wherein the distal ends are operable to connect to the syringe coupler 156. The syringe coupler 156 comprises a valve assembly with a sealing element 164 that nests within recessed area 159 of a displaceable member 158. In some embodiments, including that shown in FIG. 13, the sealing element comprises a fluid impermeable material with an aperture to selectively allow fluid to flow through the device 156. The sealing element 164 of FIG. 13 comprises a rectilinear member and is contemplated as having various shapes and sizes.

The displaceable member 158 comprises a user-interface 160 that is operable to be contacted by and receive a force from a user and a male extension 162 for receiving the second syringe 154. The syringe coupler 156 further comprises a guide member 168 within which the displaceable member is provided. The guide member 168 comprises a user-interface 178 (FIG. 15C) that is operable to be contacted by and receive a force from a user. A rotatable member 166 is provided. The rotatable member 166 of the depicted embodiment comprises a rotatable Luer lock member with a proximal end with a male fitting operable to connect to the first syringe 152, and a distal end comprising a flange with a plurality of contact surfaces for limiting rotation of the rotatable member 166 prior to activation of the device.

FIGS. 14A-14C are perspective views showing the displaceable member 158 in greater detail. As shown, the displaceable member 158 comprises a user-interface 160 operable to be acted upon by a user. In preferred embodiments, the displaceable member is displaceable in a downward direction (at least relative to FIG. 14A) and is preferably not operable to return to an initial or first position. A male extension 162 is provided on one side of the member for receiving a syringe. A recess 159 is provided on an opposing side of the displaceable member relative to the male extension 162. The recess 159 is operable to receive a sealing element, such as the sealing element 164 of FIG. 13. A channel is provided through the displaceable member 158, wherein the channel extends through the male extension 162 and into the recess 159. Preferably, a sealing element comprises an aperture that is aligned with the channel of the displaceable member 158.

As shown in FIGS. 14B-14C, a projection 170 is provided on the displaceable member 158. The projection 170 is displaceable with the member 158 and is moveable relative to at least the rotatable member 166 of an assembled device. In a first position, the projection 170 is provided in contact with a contact surface of the flange of the rotatable member 166 to prevent rotation of the member 166. This contact and related locking of the rotatable member 166 enables a first syringe to be threaded onto (and threadably removed from) the rotatable member 166 prior to activation of the assembled device. Movement of the displaceable member 158 by user activation results in displacing the projection 170 such it is not in contact with rotatable locking member 166. With rotation of the rotatable Luer lock member enabled, the member 166 is free to spin within the syringe coupler. Without resistance, a syringe connected to the rotatable Luer lock member 166 is prevented from being threadably detached from the syringe coupler even if and when a rotation is applied in an attempt to remove the syringe. It is an object of the present disclosure to provide a syringe coupler 156 that retains at least one syringe such that a user is prevented from using the first syringe for administration and is thereby only given the option of administering the mixed contents with the second syringe.

As shown in FIGS. 14A-4C, the displaceable member 158 also comprises clips or resilient projections 172a, 172b. The resilient projections 172a, 172b are operable to flex outwardly and do not substantially impede a downward movement of the displaceable member 158. When provided in a second position, however, the resilient projections 172a, 172b are secured to the guide member 168 at least in part due to an inherent restoring force of the projections. The resilient projections 172a, 172b secure the displaceable member 158 in a second position within guide member 168 through engagement of said resilient projections 172a, 172b into recesses 176a, 176b located upon guide member 168 to prevent or inhibit the displaceable member from being returned to a first position.

FIGS. 15A-15D are perspective views of a guide member 168 according to one embodiment and contemplated for use and cooperation with the displaceable member 158 is FIGS. 14A-14C. As shown, the guide member 168 comprises a central aperture 174 to permit fluid flow and to receive a rotatable Luer lock member 166 of embodiments of the disclosure. The guide member 168 is provided to slidably receive at least a portion of a displaceable member 158. As shown, the guide member 168 comprises a receiving portion 180 with first and second slot members 178a, 178b to receive a displaceable member 158. The guide member comprises a user-interface 178 that is operable to be contacted by and receive a force from a user. In certain embodiments, and as shown in FIGS. 15A-15D, the user-interface 178 is contemplated as comprising a gripping or contact surface having ridges to reduce slipping and provide ergonomic benefits.

A surface of the guide member 168 comprises a recessed area 182 in which the projection 170 of the displaceable member 158 (FIG. 14B, for example) is allowed to translate. Specifically, when the coupler is activated and the displaceable member 158 is displaced downwardly relative to the guide member 168, the projection 170 downwardly in the recessed area 182 to a second position wherein the projection 170 is not in contact with the rotatable member 166 regardless of the rotational position of the rotatable member 166.

The second position further comprises a position wherein a fluid flow channel is created. Specifically, a sealing element 164 provided within the displaceable member 158 is moved from a first position characterized by a channel of the sealing element 164 being offset from and preventing flow between inlets and outlets of interconnected syringes and a second position characterized by the channel of the sealing element 164 being provided in axial alignment with the syringe outlets and inlets.

As shown in FIGS. 15A-15B, for example, the guide member 168 further comprises recesses 176a, 176b that are operable to receive resilient projections of a displaceable member and secure the syringe coupler in a second position. The recesses are operable to prevent or at least impede a user from returning the device to a first position after activation of the syringe coupler.

FIGS. 16A-16B are perspective views of a rotatable member 166 according to one embodiment of the present disclosure. As shown, the rotatable member 166 comprises a first end with a male Luer lock 200 that provides a means of attachment to a first syringe as well as a fluid flow path through a central aperture 202 of the member 166. The male Luer lock 200 is at least partially provided within a threaded female member 204 that is operable to threadingly engage a first syringe. A bearing surface 208 is provided on an exterior of the member 166. The bearing surface 208 is operable to be provided in the central aperture 174 of the guide member 168 and contact the guide member. The bearing surface 208 of the rotatable member 166 comprises a surface upon which the member 166 can rotate (when unlocked) and contact the central aperture 174 of the guide member 168. The rotatable member 166 further comprises a flange 206 with a plurality of contact surfaces 207 to selectively prevent rotation of the rotatable member 166. Specifically, when a projection of the present disclosure (170 of FIG. 14B, for example) is provided in a first position, the projection 170 is provided in contact with at least one contact surface 207 of the flange 206 and rotation of the member 166 is prevented (at least with respect to the guide member 168). The secured nature or state of the member 166 in the first position allows a user to thread a first syringe within the threaded female member 204. When the displaceable member is displaced as shown and described herein, the projection 170 is moved away from the flange 206 of the member 166 such that rotation is unopposed and the member 166 is allowed to rotate relative to the guide member 168 and the displaceable member. This freedom of rotation prevents or at least inhibits the un-threading and removal of the first syringe as a rotation force applied to the syringe will cause a rotation of the rotatable member 166. With no significant oppositional force on the rotatable Luer lock member 166 or threaded female member 204, un-threading will not occur and the first syringe is effectively prevented from being removed from the syringe coupler. The flange 206 of the embodiment of FIGS. 16A-16B is depicted as a hexagonal flange. It will be recognized, however, that various alternative shapes and arrangements are contemplated that comprise at least one contact surface for selectively preventing rotation of the member 166.

FIG. 16B shows the distal end of the channel 202 of the rotatable member 166. As shown, the distal end 210 comprises a ramped or frustoconical shape. The angled surface(s) of the distal end 210 allow for ease of assembly of the device. Specifically, the distal end 210 is operable to communicate with a slot or ramp 171 of the displaceable member 158 (FIG. 14C, for example). The angled nature of these corresponding features allows the guide member 168 comprising the rotatable member 166 to slide relative to and be assembled with the displaceable member 158. As previously discussed, the displaceable member is contemplated as comprising a sealing member 164. In addition to facilitating ease of assembly, the communication of the distal end 210 and the ramp 171 of the guide member provides for a temporary separation of the guide member 168 and the displaceable member and avoid unwanted contact, damage, or snagging of the seal 164 during assembly. Upon full insertion of the displaceable member 158 within the guide member 168, the distal end 210 is provided proximal to the sealing member 164.

FIGS. 17A-17B are cross-sectional elevation views of a system according to an embodiment of the present disclosure. As shown and previously described, the system comprises a first syringe 152 and a second syringe 154. The syringes 152, 154 are connected to a syringe coupler comprising a displaceable member 158 with a user-interface 160, a sealing element 164, a guide member 168, and a rotatable member 166 provided at least partially within the guide member 168. The system is shown as being provided in a first position in FIG. 17A. The first position comprises a position wherein the displaceable member and associated sealing element 164 are provided offset from a central axis and passageway of the rotatable member 166. Specifically, a fluid flow path 190*a* of the second syringe 154, the male extension of the displaceable member 158, and the sealing member 164 is offset from and not in communication with a fluid flow path 190*b* of the first syringe 152 and the rotatable member 166. Fluid and gaseous vapor flow between syringes is thus prevented.

FIG. 17B depicts the system in a second position wherein the displaceable member 158 has been displaced by application of force upon the user-interface 160 (for example). As shown, fluid pathway 190*a* of FIG. 7A and related components have been displaced such that a continuous fluid pathway 190 is provided and fluid flow between the first syringe 152 and second syringe 154 is enabled. Mixing of contents is thus enabled, wherein plunger rods (not shown in FIGS. 17A-17B) associated with the first and second syringes are operable to force contents between the syringes.

Systems, devices and methods of the present disclosure are not limited to any particular therapeutic agent(s), solution(s), suspension(s), gas(es), or a combination thereof. Various embodiments comprise features and sealing elements for preventing materials in at least one syringe from escaping or migrating to another syringe. In some embodiments, for example, it is contemplated that that one or more non-lyophilized materials are provided in syringes of the present disclosure. In some embodiments, a gas (e.g. Nitrogen or Argon gas) is provided in a syringe for mixing with contents of a second syringe. Gas may be desirable, for example, to be provided with an active pharmaceutical ingredient to preserve that ingredient during storage. Sealing elements of the present disclosure are operable to and suitable for maintaining gas in a syringe and preventing unwanted migration of that gas. Sealing elements are also suitable and operable for preventing escape or flow of liquids and solids.

In some embodiments, mixing syringe systems of the present disclosure comprise gas-impermeable materials to prevent gas permeation and migration. However, in certain preferred embodiments, a first syringe 152 is initially provided with a liquid formulation component (i.e. liquid or flowable material) such as a polymer-solvent system and a second syringe is provided with an API, which may, in some non-limiting instances, be present as a lyophilized power. In such embodiments, the contents are stored separately with each respective syringe, which are interconnected to the syringe coupler with the displaceable member provided in the first position (FIG. 17A). To administer a therapeutic agent, the displaceable member is depressed or otherwise activated, creating the fluid-flow pathway 190 of FIG. 17B. Repetitive mixing may then be performed by forcing the polymer-solvent of the first syringe 152 into the second syringe that comprises the API, forcing the contents back to the first syringe, and repeating the process until desired mixing is achieved. As discussed, the second position of FIG. 17B is characterized by the presence of a fluid flow path between the two syringes, as well as by the disengagement of the displaceable member 158 and the rotatable member 166. Specifically, the second position (FIG. 17B) comprises a position in which the rotatable member 166 is free to rotate within the syringe coupler and the first syringe 152 is prevented from unthreading or detachment. Accordingly, the second syringe preferably comprising the mixed or prepared agent is detachable for use as an injection syringe while the first syringe is inoperable for such purposes.

As disclosed herein, the syringe mixing system of the invention may comprise methods and systems for mixing components of a pharmaceutical composition or formulation comprising an API useful in the treatment in a disease or disorder in a patient. In some embodiments, the syringe mixing system comprises a first syringe containing a first gas, liquid, or solid composition and a second syringe containing a second gas, liquid, or solid composition. Upon activation of the syringe connector from a first, closed position to a second, open position, the first gas, liquid, or solid composition of the first syringe may be intermixed with the second gas, liquid, or solid composition of the second syringe (or vice versa) until a desired intermixed composition is formed. In some instances, the first or second syringe (but not both) may contain a gas component which may be an inert or volatile gas or gas vapor. In some instances, the first and second syringe may contain an aqueous based or organic based liquid which forms a solution, suspension, or both. In some further instances of the disclosed invention, the first syringe may comprise liquid formulation component or a solvent system which may, in some non-limiting examples, contain a biodegradable polymer dissolved or suspended within an aqueous, organic, or intermixed aqueous-organic solvent system, which may further contain additional co-solvents. In some instances, the first or second syringe (but not both) may contain a solid which may be an API useful in the treatment of a disease or disorder or amelioration of a symptom thereof. In some further instances, the solid may be a lyophilized powder, semi-solid particulate(s), or solid particulate(s) of varying sizes, shapes, and characteristics (e.g. specific surface area for example). Yet, further still, in some other non-limiting instances, the first or second syringe of the syringe device system may comprise a lyophilized powder, semi-solid particulate(s), or solid particulate(s) of varying sizes, shapes, and characteristics (e.g. specific surface area for example) which may be prepared and/or stored within the first or second syringe within the presence of a gas of choice, i.e. both lyophilized powder and gas are contained within the first or second syringe prior to mixing said components with the components stored within the opposing syringe, which may be, but is not necessarily limited to, a liquid of interest.

As disclosed herein, the syringe mixing system of the invention may comprise methods and systems for mixing components of a pharmaceutical composition or formulation comprising an API useful in the treatment of a disease or condition in a patient. Such a syringe mixing system may be referred to as a "prefilled syringe mixing system", wherein the syringes of the syringe mixing system are prefilled with components of a pharmaceutical composition or formulation that are then mixed together using the syringe mixing system as described herein, such that the mixed pharmaceutical composition or formulation can then be administered to a patient in need of such pharmaceutical composition or formulation. In some embodiments of the invention, the syringe mixing device (prefilled syringe mixing system) may comprise a pharmaceutical formulation comprising: (a) an API, which is contained within the first syringe, and (b) a biodegradable polymer-solvent system contained within the second syringe, which may be intermixed upon activation of the syringe connector by a user such as to prepare a medication or medicament useful in the treatment of a disease or condition by administration of the mixed formulation into a patient in need thereof. The syringe mixing system can be used to store and then mix for administration any pharmaceutical composition or formulation that would benefit from the advantages of the inventive syringe mixing system, and the disease or condition to be treated will naturally depend on the drug or therapeutic agent included in the pharmaceutical composition or formulation.

In some embodiments, the API is a Gonadotrophin Releasing Hormone (GhRH) agonist or antagonist or a pharmaceutically acceptable salt thereof. Diseases or conditions that may be treated with a GnRH agonist or antagonist or a pharmaceutically acceptable salt thereof may include, but are not limited to, certain types of cancers, central precocious puberty (CPP), endometriosis, or uterine fibroids. In some instances, a cancer that may be treated with a GnRH agonist or antagonist or a pharmaceutically acceptable salt thereof may include but is not limited to prostate cancer (including but not limited to advanced prostate cancer) or breast cancer.

Leuprolide, as known as leuprorelin, is a synthetic peptide analog that acts as a "super agonist" upon pituitary GnRH receptors. GnRH agonists, such as leuprolide or a pharmaceutically acceptable salt thereof (such as leuprolide acetate), may be used in the treatment of prostate cancer (including advanced prostate cancer) in adult males, HR-positive breast cancer (including, but not limited, to HR-positive, human epidermal growth factor receptor 2 (HER2)-negative breast cancer) and CPP. Administration of GnRH agonists (or GnRH) leads to downregulation of GnRH receptor activity, which in turn downregulates GnRH-dependent secretion of gonadotropins, including but not limited to, luteinizing hormone (LH) and follicle-stimulating hormone (FSH). Downregulation of LH and FSH leads to subsequent down-regulation of secondary sex-hormones, including but not limited to, testosterone and estradiol. Testosterone is a key metabolite in driving prostate cancer development and progression in adult males. As such, the reduction of serum testosterone levels is a useful clinical approach for slowing or inhibiting the growth of prostate cancer. Likewise, clinical approaches that modulate hormone activity and/or synthesis, particularly that of estrogens (e.g. estradiol), are useful for slowing or inhibiting the growth of hormone receptor-positive (HR-positive) breast cancer. Controlled release formulations for the extended release of leuprolide useful in the treatment of the prostate cancer in adult males, breast cancer, and CPP in pediatric patients 2 years old or older have been developed. Controlled release formulations using flowable biodegradable polymer based compositions for sustained, extended release of leuprolide or pharmaceutically acceptable salts thereof have been described, by way of example, in U.S. Pat. Nos. 6,565,874 and 8,470,359, WO 2020/2404170, and WO 2020/217170, each of which are incorporated herein by reference in their entireties.

As disclosed herein, the syringe device or mixing system may be used to subcutaneously administer an API to a patient in need thereof. In some embodiments, the API is a GnRH agonist or antagonist or a pharmaceutically acceptable salt thereof and the patient may suffer from prostate cancer, hormone receptor-positive breast cancer, or CPP. In some embodiments, the method of administering the GnRH agonist or antagonist or the pharmaceutically acceptable salt thereof comprises mixing a unit dose of the GnRH agonist or antagonist or the pharmaceutically acceptable salt thereof with a liquid formulation component to form a reconstituted pharmaceutical composition using the syringe-to-syringe mixing system; and administering the reconstituted pharmaceutical composition to the patient via subcutaneous injection. In some embodiments, the syringe-to-syringe mixing system comprises a first syringe barrel comprising the GnRH agonist or antagonist or the pharmaceutically acceptable salt thereof, a second syringe barrel comprising the liquid formulation component, and a syringe coupler comprising a displaceable member, wherein the displaceable member comprises a seal with a flow port that is offset from an outlet of at least one of the first syringe barrel and the second syringe barrel when the displaceable member is provided in a first position, and wherein the flow port is aligned with the outlet of the first syringe barrel and the second syringe barrel when the displaceable member is provided in a second position, and wherein the displaceable member is displaceable in a direction that is substantially perpendicular to a longitudinal axis of at least one of the first syringe barrel and the second syringe barrel. The mixing comprises applying a force to a user-interface to move the displaceable seal from the first position to the second position and applying force to a plunger positioned in the first syringe barrel and a plunger positioned in the second syringe barrel in an alternating manner to mix the contents of the first syringe barrel and the second syringe barrel. In some instances, the GnRH agonist or antagonist or the pharmaceutically acceptable salt thereof is leuprolide or a pharmaceutically acceptable salt thereof, such as leuprolide acetate.

In one embodiment, a syringe device system comprises a composition, which when formulated according to the methods of using the syringe device system as described herein to intermix two separated components of the composition prior to administration, may be useful in the palliative treatment of prostate cancer, including the palliative treatment of advanced prostate cancer in an adult male patient, when administered by subcutaneous injection about once every month (once per month) to reduce the patient's serum testosterone level to less than or equal to 0.5 ng/mL. According to this embodiment, the syringe device system comprises a first syringe containing an amount of a GnRH agonist or antagonist or a pharmaceutically acceptable salt thereof. In some instances, the syringe device system comprises a first syringe containing an amount of lyophilized leuprolide or a pharmaceutically acceptable salt thereof, such as lyophilized leuprolide acetate. In some instances, the amount of leuprolide or a pharmaceutically acceptable salt thereof in the delivered reconstituted product may be about 7.0 mg leuprolide free base equivalent. In some instances, the amount of leuprolide acetate in the delivered reconstituted product may be about 7.5 mg. As used herein, the term "free base equivalent" may refer to the conjugate base or deprotonated form of an amine containing compound or substance. For instance, about 7.0 mg of leuprolide represents the free base equivalent of about 7.5 mg of leuprolide acetate. According to this embodiment, the syringe device system comprises a second syringe containing an amount of a polymer-solvent system comprising an amount of a biodegradable polymer, which in some instances is a poly(D, L-lactide-co-glycolide) acid-initiated (i.e. PLGH) polymer, dissolved in a biocompatible solvent, which in some instances is NMP. In some instances, the biodegradable PLGH polymer may comprise a lactide to glycolide ratio of about 50:50. In some instances, the PLGH polymer may compromise a copolymer containing at least one carboxyl end group. In some instances, the PLGH polymer has a weight average molecular weight from about 31 kDa to about 45 kDa. In some instances, the amount of PLGH polymer in the delivered reconstituted product may be about 82.5 mg. In some instances, the amount of NMP in the delivered reconstituted product is about 160 mg. The term "weight average molecular weight," unless otherwise specified, means a weight average molecular weight as measured by a conventional gel permeation chromatography (GPC) instrument (such as an Agilent 1260 Infinity Quaternary LC with Agilent G1362A Refractive Index Detector) utilizing polystyrene standards and tetrahydrofuran (THF) as the solvent.

According to the methods of activating the syringe device system, as disclosed herein, the user, after first allowing the pre-assembled syringe device system to equilibrate to room temperature and then removing it from its packaging, applies force to the user-interface portions 52 and 57 of the displaceable member 50 and the guide member 56, respectively, to activate the syringe coupler from the first closed position to the second open position. The user then applies a force to the second plunger disposed slidably within the second syringe to transfer the polymer-solvent system housed within the internal chamber of the second syringe barrel through the open, activated syringe coupler and into the internal chamber of the first syringe housing the lyophilized leuprolide acetate. Upon contact of the polymer-solvent system with the lyophilized leuprolide acetate, the leuprolide acetate will largely remain in suspension, thus requiring mixing with the polymer-solvent system to ensure that a homogeneous suspension is formed prior to administration. The user then applies a force to the first plunger disposed slidably within the first syringe to transfer the partially to fully mixed components back through the open syringe coupler and into the second syringe. The user will continue mixing the contents back and forth from the first and second syringes for between about 15 seconds and two minutes. In some instances, mixing is contemplated as continuing for about 25 seconds, about 45 seconds, or about 1 minute, equivalent to approximately 30-90 full back-and-forth cycles (and in some preferred embodiments, about 60 full back-and-forth cycles) to ensure that the lyophilized leuprolide acetate is fully suspended within the polymer-solvent system. The fully formulated composition is subsequently displaced into the second syringe at a final injection volume of about 0.25 mL and administered formulation weight of about 250 mg. The user then disconnects the second syringe containing the therapeutic formulation from the syringe device by de-threading attachment to the male extension 54 upon the displaceable member 50 of the syringe connector. The user then attaches a needle, for example an 18 G to 20 G needle, to the distal dispensing outlet of the second syringe. The user then subcutaneously administers the full formulation dose to an adult male prostate cancer patient in need of treatment thereof.

According to the methods of administering the GnRH agonist or antagonist or a pharmaceutically acceptable salt thereof to a patient with prostate cancer using the syringe device system disclosed herein, the method comprises subcutaneously administering at least one injection of a pharmaceutic composition comprising a unit dose of a GnRH agonist or antagonist or a pharmaceutically acceptable salt thereof, once every month (once per month), to the patient to suppress the patient's serum testosterone level to less than or equal to 0.5 ng/ml. Prior to the administering, the pharmaceutic composition is reconstituted using the syringe device system comprising a first syringe barrel comprising the GnRH agonist or antagonist or a pharmaceutically acceptable salt thereof and a second syringe barrel comprising a liquid formulation component, the first and second syringe barrels being interconnected via a syringe coupler comprising a displaceable seal, wherein the displaceable seal being operable to be axially displaced from a first position to a second position by a force applied to a plunger of the first syringe barrel, and wherein the first position comprises a position in which material transfer through the syringe coupler is occluded, and the second position comprises a position in which at least a portion of the displaceable seal is not secured to an interior surface of the syringe coupler and material transfer through the syringe coupler is permitted. The pharmaceutic composition is reconstituted by applying a force to a user-interface to move the displaceable seal from the first position to the second position and applying force to a plunger positioned in the first syringe barrel and a plunger positioned in the second syringe barrel in an alternating manner to mix contents of the first syringe barrel and the second syringe barrel. In some instances, the GnRH agonist or antagonist or the pharmaceutically acceptable salt thereof is leuprolide or a pharmaceutically acceptable salt thereof, such as leuprolide acetate. In some instances, the GnRH agonist or antagonist or the pharmaceutically acceptable salt thereof is leuprolide or a pharmaceutically acceptable salt thereof, such as leuprolide acetate. In some instances, the pharmaceutical composition comprises about 7.5 mg of leuprolide acetate and N-methyl-2-pyrrolidone and a 50:50 poly(lactic acid-co-glycolic acid) (PLGA) copolymer having a weight average molecular weight from about 31 kDa to about 45 kDa and at least one terminal carboxylic acid end group as the liquid formulation component.

In another embodiment, a syringe device system comprises a composition, which when formulated according to the methods of using the syringe device system as described herein to intermix two separated components of the composition prior to administration, may be useful in the palliative treatment of prostate cancer, including the palliative treatment of advanced prostate cancer in an adult male patient, when administered by subcutaneous injection about once every three months (once per three months) to reduce the patient's serum testosterone level to less than or equal to 0.5 ng/mL. According to this embodiment, the syringe device system comprises a first syringe containing an amount of a GnRH agonist or antagonist or a pharmaceutically acceptable salt thereof. In some instances, the syringe device system comprises a first syringe containing an amount of lyophilized leuprolide or a pharmaceutically acceptable salt thereof, such as lyophilized leuprolide acetate. In some instances, the amount of leuprolide or a pharmaceutically acceptable salt thereof in the delivered reconstituted product may be about 21.0 mg leuprolide free base equivalent. In some instances, the amount of leuprolide acetate in the delivered reconstituted product may be about 22.5 mg. According to this embodiment, the syringe device system comprises a second syringe containing an amount of a polymer-solvent system comprising an amount of a biodegradable polymer, which in some instances is a poly(D, L-lactide-co-glycolide) (i.e. PLG) polymer dissolved in a biocompatible solvent, which in some instances is NMP. In some instances, the biodegradable PLG polymer may comprise a lactide to glycolide ratio of about 75:25. In some instances, the PLG polymer may be initiated with hexanediol. In some instances, the PLG polymer may compromise a copolymer containing two primary hydroxyl end groups. In some instances, the PLG polymer has a weight average molecular weight range of about 17 kDa to about 21 kDa. In some instances, the amount of PLG polymer in the delivered reconstituted product may be about 158.6 mg. In some instances, the amount of NMP in the delivered reconstituted product is about 193.9 mg.

According to the methods of activating the syringe device system, as disclosed herein, the user, after first allowing the pre-assembled syringe device system to equilibrate to room temperature and then removing it from its packaging, applies force to the user-interface portions 52 and 57 of the displaceable member 50 and the guide member 56, respectively, to activate the syringe coupler from the first closed position to the second open position. The user then applies a force to the second plunger disposed slidably within the second syringe to transfer the polymer-solvent system housed within the internal chamber of the second syringe barrel through the open, activated syringe coupler and into the internal chamber of the first syringe housing the lyophilized leuprolide acetate. Upon contact of the polymer-solvent system with the lyophilized leuprolide acetate, the leuprolide acetate will largely remain in suspension, thus requiring mixing with the polymer-solvent system to ensure that a homogeneous suspension is formed prior to administration. The user then applies a force to the first plunger disposed slidably within the first syringe to transfer the partially to fully mixed components back through the open syringe coupler and into the second syringe. The user will continue mixing the contents back and forth from the first and second syringes, in some instances for about 1 minute, equivalent to approximately 60 full back-and-forth cycles to ensure that the lyophilized leuprolide acetate is fully suspended within the polymer-solvent system. The fully formulated composition is subsequently displaced into the second syringe at a final injection volume of about 0.375 mL and administered formulation weight of about 375 mg. The user then disconnects the second syringe containing the therapeutic formulation from the syringe device by de-threading attachment to the male extension 54 upon the displaceable member 50 of the syringe connector. The user then attaches a needle, for example an 18 G to 20 G needle, to the distal dispensing outlet of the second syringe. The user then subcutaneously administers the formulation dose to an adult male prostate cancer patient in need of treatment thereof.

According to the methods of administering the GnRH agonist or antagonist or a pharmaceutically acceptable salt thereof to a patient with prostate cancer using the syringe device system disclosed herein, the method comprises subcutaneously administering at least one injection of a pharmaceutic composition comprising a unit dose of a GnRH agonist or antagonist or a pharmaceutically acceptable salt thereof, once every three months (once per three months), to the patient to suppress the patient's serum testosterone level to less than or equal to 0.5 ng/ml. Prior to the administering, the pharmaceutic composition is reconstituted using the syringe device system comprising a first syringe barrel comprising the GnRH agonist or antagonist or a pharmaceutically acceptable salt thereof and a second syringe barrel comprising a liquid formulation component, the first and second syringe barrels being interconnected via a syringe coupler comprising a displaceable seal, wherein the displaceable seal being operable to be axially displaced from a first position to a second position by a force applied to a plunger of the first syringe barrel, and wherein the first position comprises a position in which material transfer through the syringe coupler is occluded, and the second position comprises a position in which at least a portion of the displaceable seal is not secured to an interior surface of the syringe coupler and material transfer through the syringe coupler is permitted. The pharmaceutic composition is reconstituted by applying a force to a user-interface to move the displaceable seal from the first position to the second position and applying force to a plunger positioned in the first syringe barrel and a plunger positioned in the second syringe barrel in an alternating manner to mix contents of the first syringe barrel and the second syringe barrel. In some instances, the GnRH agonist or antagonist or the pharmaceutically acceptable salt thereof is leuprolide or a pharmaceutically acceptable salt thereof, such as leuprolide acetate. In some instances, the GnRH agonist or antagonist or the pharmaceutically acceptable salt thereof is leuprolide or a pharmaceutically acceptable salt thereof, such as leuprolide acetate. In some instances, the pharmaceutical composition comprises about 22.5 mg of leuprolide acetate and N-methyl-2-pyrrolidone, and a 75:25 poly(lactide-co-glycolide) (PLG) copolymer having a weight average molecular weight from about 17 kDa to about 21 kDa and end groups that are hydroxyl-terminated as the liquid formulation component.

In yet another embodiment, a syringe device system comprises a composition, which when formulated according to the methods of using the syringe device system as described herein to intermix two separated components of the composition prior to administration, may be useful in the palliative treatment of prostate cancer, including the palliative treatment of advanced prostate cancer in an adult male patient, when administered by subcutaneous injection about once every four months (once per four months) to reduce the patient's serum testosterone level to less than or equal to 0.5 ng/mL. According to this embodiment, the syringe device system comprises a first syringe containing an amount of a GnRH agonist or antagonist or a pharmaceutically acceptable salt thereof. In some instances, the syringe device system comprises a first syringe containing an amount of lyophilized leuprolide or a pharmaceutically acceptable salt thereof, such as lyophilized leuprolide acetate. In some instances, the amount of leuprolide or a pharmaceutically acceptable salt thereof in the delivered reconstituted product may be about 28.0 mg leuprolide free base equivalent. In some instances, the amount of leuprolide acetate in the delivered reconstituted product may be about 30.0 mg. According to this embodiment, the syringe device system comprises a second syringe containing an amount of a polymer-solvent system comprising an amount of a biodegradable polymer, which in some instances is a poly(D,L-lactide-co-glycolide) (i.e. PLG) polymer formulation dissolved in a biocompatible solvent, which in some instances is NMP. In some instances, the biodegradable PLG polymer may comprise a lactide to glycolide ratio of about 75:25. In some instances, the PLG polymer may be initiated with hexanediol. In some instances, the PLG polymer may compromise a copolymer containing two primary hydroxyl end groups. In some instances, the PLG polymer has a weight average molecular weight range of about 17 kDa to about 21 kDa. In some instances, the amount of PLG polymer in the delivered reconstituted product may be about 211.5 mg. In some instances, the amount of NMP in the delivered reconstituted product is about 258.5 mg.

According to the methods of activating the syringe device system, as disclosed herein, the user, after first allowing the pre-assembled syringe device system to equilibrate to room temperature and then removing it from its packaging, applies force to the user-interface portions 52 and 57 of the displaceable member 50 and the guide member 56, respectively, to activate the syringe coupler from the first closed position to the second open position. The user then applies a force to the second plunger disposed slidably within the second syringe to transfer the polymer-solvent system housed within the internal chamber of the second syringe barrel through the open, activated syringe coupler and into the internal chamber of the first syringe housing the lyophilized leuprolide acetate. Upon contact of the polymer-solvent system with the lyophilized leuprolide acetate, the leuprolide acetate will largely remain in suspension, thus requiring mixing with the polymer-solvent system to ensure that a homogeneous suspension is formed prior to administration. The user then applies a force to the first plunger disposed slidably within the first syringe to transfer the partially to fully mixed components back through the open syringe coupler and into the second syringe. The user will continue mixing the contents back and forth from the first and second syringes, in some instances for about 1 minute, equivalent to approximately 60 full back-and-forth cycles to ensure that the lyophilized leuprolide acetate is fully suspended within the polymer-solvent system. The fully formulated composition is subsequently displaced into the second syringe at a final injection volume of about 0.5 mL and administered formulation weight of about 500 mg. The user then disconnects the second syringe containing the therapeutic formulation from the syringe device by de-threading attachment to the male extension 54 upon the displaceable member 50 of the syringe connector. The user then attaches a needle, for example an 18 G to 20 G needle, to the distal dispensing outlet of the second syringe. The user then subcutaneously administers the full formulation dose to an adult male prostate cancer patient in need of treatment thereof.

According to the methods of administering the GnRH agonist or antagonist or a pharmaceutically acceptable salt thereof to a patient with prostate cancer using the syringe device system disclosed herein, the method comprises subcutaneously administering at least one injection of a pharmaceutic composition comprising a unit dose of a GnRH agonist or antagonist or a pharmaceutically acceptable salt thereof, once every four months (once per four months), to the patient to suppress the patient's serum testosterone level to less than or equal to 0.5 ng/ml. Prior to the administering, the pharmaceutic composition is reconstituted using the syringe device system comprising a first syringe barrel comprising the GnRH agonist or antagonist or a pharmaceutically acceptable salt thereof and a second syringe barrel comprising a liquid formulation component, the first and second syringe barrels being interconnected via a syringe coupler comprising a displaceable seal, wherein the displaceable seal being operable to be axially displaced from a first position to a second position by a force applied to a plunger of the first syringe barrel, and wherein the first position comprises a position in which material transfer through the syringe coupler is occluded, and the second position comprises a position in which at least a portion of the displaceable seal is not secured to an interior surface of the syringe coupler and material transfer through the syringe coupler is permitted. The pharmaceutic composition is reconstituted by applying a force to a user-interface to move the displaceable seal from the first position to the second position and applying force to a plunger positioned in the first syringe barrel and a plunger positioned in the second syringe barrel in an alternating manner to mix contents of the first syringe barrel and the second syringe barrel. In some instances, the GnRH agonist or antagonist or the pharmaceutically acceptable salt thereof is leuprolide or a pharmaceutically acceptable salt thereof, such as leuprolide acetate. In some instances, the GnRH agonist or antagonist or the pharmaceutically acceptable salt thereof is leuprolide or a pharmaceutically acceptable salt thereof, such as leuprolide acetate. In some instances, the pharmaceutical composition comprises about 30 mg of leuprolide acetate and N-methyl-2-pyrrolidone, and a 75:25 poly(lactide-co-glycolide) (PLG) copolymer having a weight average molecular weight from about 17 kDa to about 21 kDa and end groups that are hydroxyl-terminated as the liquid formulation component.

In yet another embodiment of the invention, the syringe device system comprises a composition, which when formulated according to the methods of using the syringe device system as described herein to intermix two separated components of the composition prior to administration, may be useful in the palliative treatment of prostate cancer, including the palliative treatment of advanced prostate cancer in an adult male patient, when administered by subcutaneous injection about once every six months (once per six months) to reduce the patient's serum testosterone level to less than or equal to 0.5 ng/mL. According to this embodiment, the syringe device system comprises a first syringe containing an amount of a GnRH agonist or antagonist or a pharmaceutically acceptable salt thereof. In some instances, the syringe device system comprises a first syringe containing an amount of lyophilized leuprolide or a pharmaceutically acceptable salt thereof, such as lyophilized leuprolide acetate. In some instances, the amount of leuprolide or a pharmaceutically acceptable salt thereof in the delivered reconstituted product may be about 42.0 mg leuprolide free base equivalent. In some instances, the amount of leuprolide acetate in the delivered reconstituted product may be about 45.0 mg. According to this embodiment, the syringe device system comprises a second syringe containing an amount of a polymer-solvent system comprising an amount of a biodegradable polymer, which in some instances is a poly(D, L-lactide-co-glycolide) (i.e. PLG) polymer formulation dissolved in a biocompatible solvent, which in some instances is NMP. In some instances, the biodegradable PLG polymer may comprise a lactide to glycolide ratio of about 85:15. In some instances, the PLG polymer may be initiated with hexanediol. In some instances, the PLG polymer may compromise a copolymer containing two primary hydroxyl end groups. In some instances, the PLG polymer has a weight average molecular weight range of about 20 kDa to about 26 kDa. In some instances, the amount of PLG polymer in the delivered reconstituted product may be about 165 mg. In some instances, the amount of NMP in the delivered reconstituted product is about 165 mg.

According to the methods of activating the syringe device system, as disclosed herein, the user, after first allowing the pre-assembled syringe device system to equilibrate to room temperature and then removing it from its packaging, applies force to the user-interface portions 52 and 57 of the displaceable member 50 and the guide member 56, respectively, to activate the syringe coupler from the first closed position to the second open position. The user then applies a force to the second plunger disposed slidably within the second syringe to transfer the polymer-solvent system housed within the internal chamber of the second syringe barrel through the open, activated syringe coupler and into the internal chamber of the first syringe housing the lyophilized leuprolide acetate. Upon contact of the polymer-solvent system with the lyophilized leuprolide acetate, the leuprolide acetate will largely remain in suspension, thus requiring mixing with the polymer-solvent system to ensure that a homogeneous suspension is formed prior to administration. The user then applies a force to the first plunger disposed slidably within the first syringe to transfer the partially to fully mixed components back through the open syringe coupler and into the second syringe. The user will continue mixing the contents back and forth from the first and second syringes, in some instances for about 1 minute, equivalent to approximately 60 full back-and-forth cycles to ensure that the lyophilized leuprolide acetate is fully suspended within the polymer-solvent system. The fully formulated composition is subsequently displaced into the second syringe at a final injection volume of about 0.375 mL and administered formulation weight of about 375 mg. The user then disconnects the second syringe containing the therapeutic formulation from the syringe device by de-threading attachment to the male extension 54 upon the displaceable member 50 of the syringe connector. The user then attaches a needle, for example an 18 G to 20 G needle, to the distal dispensing outlet of the second syringe. The user then subcutaneously administers the full formulation dose to an adult male prostate cancer patient in need of treatment thereof.

According to the methods of administering the GnRH agonist or antagonist or a pharmaceutically acceptable salt thereof to a patient with prostate cancer using the syringe device system disclosed herein, the method comprises subcutaneously administering at least one injection of a pharmaceutic composition comprising a unit dose of a GnRH agonist or antagonist or a pharmaceutically acceptable salt thereof, once every six months (once per six months), to the patient to suppress the patient's serum testosterone level to less than or equal to 0.5 ng/ml. Prior to the administering, the pharmaceutic composition is reconstituted using the syringe device system comprising a first syringe barrel comprising the GnRH agonist or antagonist or a pharmaceutically acceptable salt thereof and a second syringe barrel comprising a liquid formulation component, the first and second syringe barrels being interconnected via a syringe coupler comprising a displaceable seal, wherein the displaceable seal being operable to be axially displaced from a first position to a second position by a force applied to a plunger of the first syringe barrel, and wherein the first position comprises a position in which material transfer through the syringe coupler is occluded, and the second position comprises a position in which at least a portion of the displaceable seal is not secured to an interior surface of the syringe coupler and material transfer through the syringe coupler is permitted. The pharmaceutic composition is reconstituted by applying a force to a user-interface to move the displaceable seal from the first position to the second position and applying force to a plunger positioned in the first syringe barrel and a plunger positioned in the second syringe barrel in an alternating manner to mix contents of the first syringe barrel and the second syringe barrel. In some instances, the GnRH agonist or antagonist or the pharmaceutically acceptable salt thereof is leuprolide or a pharmaceutically acceptable salt thereof, such as leuprolide acetate. In some instances, the GnRH agonist or antagonist or the pharmaceutically acceptable salt thereof is leuprolide or a pharmaceutically acceptable salt thereof, such as leuprolide acetate.

In some instances, the pharmaceutical composition comprises about 45 mg of leuprolide acetate and N-methyl-2-pyrrolidone, and an 85:15 poly(lactide-co-glycolide) (PLG) copolymer having a weight average molecular weight from about 20 kDa to about 26 kDa and end groups that are hydroxyl-terminated as the liquid formulation component.

In yet another embodiment, a syringe device system comprises a composition, which when formulated according to the methods of using the syringe device system as described herein to intermix two separated components of the composition prior to administration, may be useful in suppressing ovarian function in a patient with HR-positive breast cancer. The composition may further be useful in suppressing one or more of the patient's estradiol (E2) level to less than 20 pg/mL, the patient's follicle stimulating hormone (FSH) level to less than 40 IU/L, and patient's mean serum luteinizing hormone (LH) level. In some instances, the composition may be administered concurrently with one or more other therapeutic treatments for HR-positive breast cancer, including, but not limited to endocrine therapy, chemotherapy, and/or radiotherapy. In some instances, the composition is administered by subcutaneous injection about once every three months (once per three months). According to this embodiment, the syringe device system comprises a first syringe containing an amount of a GnRH agonist or antagonist or a pharmaceutically acceptable salt thereof. In some instances, the syringe device system comprises a first syringe containing an amount of lyophilized leuprolide or a pharmaceutically acceptable salt thereof, such as lyophilized leuprolide acetate. In some instances, the amount of leuprolide or a pharmaceutically acceptable salt thereof in the delivered reconstituted product may be about 26 mg to about 30 mg, preferably 28 mg leuprolide free base equivalent. In some instances, the amount of leuprolide acetate in the delivered reconstituted product may be about 28 mg to about 32 mg, preferably 30 mg. According to this embodiment, the syringe device system comprises a second syringe containing an amount of a polymer-solvent system comprising an amount of a biodegradable polymer, which in some instances is a poly(D,L-lactide-co-glycolide) (i.e. PLG) polymer formulation dissolved in a biocompatible solvent, which in some instances is NMP. In some instances, the biodegradable PLG polymer may comprise a lactide to glycolide ratio of about 70:30 to about 80:20, preferably about 75:25. In some instances, the PLG polymer may be initiated with hexanediol. In some instances, the PLG polymer may compromise a copolymer containing two primary hydroxyl end groups. In some instances, the PLG polymer may be initiated with dodecanol. In some instances, the PLG polymer may compromise a copolymer containing a hydroxyl end group and an ester end group. In some instances, the PLG polymer has a weight average molecular weight range of about 15 kDa to about 45 kDa, preferably about 17 kDa to about 21 kDa. In some instances, the amount of PLG polymer in the delivered reconstituted product may be about 158.6 mg. In some instances, the amount of NMP in the delivered reconstituted product is about 193.9 mg.

According to the methods of activating the syringe device system, as disclosed herein, the user, after first allowing the pre-assembled syringe device system to equilibrate to room temperature and then removing it from its packaging, applies force to the user-interface portions 52 and 57 of the displaceable member 50 and the guide member 56, respectively, to activate the syringe coupler from the first closed position to the second open position. The user then applies a force to the second plunger disposed slidably within the second syringe to transfer the polymer-solvent system housed within the internal chamber of the second syringe barrel through the open, activated syringe coupler and into the internal chamber of the first syringe housing the lyophilized leuprolide acetate. Upon contact of the polymer-solvent system with the lyophilized leuprolide acetate, the leuprolide acetate will largely remain in suspension, thus requiring mixing with the polymer-solvent system to ensure that a homogeneous suspension is formed prior to administration. The user then applies a force to the first plunger disposed slidably within the first syringe to transfer the partially to fully mixed components back through the open syringe coupler and into the second syringe. The user will continue mixing the contents back and forth from the first and second syringes, in some instances for about 1 minute, equivalent to approximately 60 full back-and-forth cycles to ensure that the lyophilized leuprolide acetate is fully suspended within the polymer-solvent system. The fully formulated composition is subsequently displaced into the second syringe at a final injection volume of about 0.375 mL and administered formulation weight of about 375 mg to about 400 mg. The user then disconnects the second syringe containing the therapeutic formulation from the syringe device by de-threading attachment to the male extension 54 upon the displaceable member 50 of the syringe connector. The user then attaches a needle, for example a 18 G to 20 G needle, to the distal dispensing outlet of the second syringe. The user then subcutaneously administers the full formulation dose to an adult breast cancer patient in need of treatment thereof.

According to the methods of administering the GnRH agonist or antagonist or a pharmaceutically acceptable salt thereof to a patient with hormone receptor-positive breast cancer using the syringe device system disclosed herein, the method comprises subcutaneously administering at least one injection of a pharmaceutic composition comprising a unit dose of a GnRH agonist or antagonist or a pharmaceutically acceptable salt thereof, once every three months (once per three months), to the patient to suppress the patient's ovarian function. In some instances, administering the at least one injection of the pharmaceutic composition comprising a unit dose of a GnRH agonist or antagonist or a pharmaceutically acceptable salt thereof, once every three months, to the patient suppresses one or more of the patient's estradiol (E2) level to less than 20 pg/mL, the patient's follicle stimulating hormone (FSH) level to less than 40 IU/L, and patient's mean serum luteinizing hormone (LH) level. Prior to the administering, the pharmaceutic composition is reconstituted using the syringe device system comprising a first syringe barrel comprising the GnRH agonist or antagonist or a pharmaceutically acceptable salt thereof and a second syringe barrel comprising a liquid formulation component, the first and second syringe barrels being interconnected via a syringe coupler comprising a displaceable seal, wherein the displaceable seal being operable to be axially displaced from a first position to a second position by a force applied to a plunger of the first syringe barrel, and wherein the first position comprises a position in which material transfer through the syringe coupler is occluded, and the second position comprises a position in which at least a portion of the displaceable seal is not secured to an interior surface of the syringe coupler and material transfer through the syringe coupler is permitted. The pharmaceutic composition is reconstituted by applying a force to a user-interface to move the displaceable seal from the first position to the second position and applying force to a plunger positioned in the first syringe barrel and a plunger positioned in the second syringe barrel in an alternating manner to mix contents of the first syringe barrel and the second syringe barrel. In some instances, the GnRH agonist or antagonist or the pharmaceutically acceptable salt thereof is leuprolide or a pharmaceutically acceptable salt thereof, such as leuprolide acetate. In some instances, the pharmaceutical composition comprises about 30 mg of leuprolide acetate and N-methyl-2-pyrrolidone and a 75:25 poly(lactide-co-glycolide) (PLG) copolymer having a weight average molecular weight from about 17 kDa to about 21 kDa and one distal end group that is hydroxyl-terminated and the other distal end group that is either hydroxyl-terminated or ester-terminated as the liquid formulation component.

In yet another embodiment of the invention, the syringe device system comprises a composition, which when formulated according to the methods of using the syringe device system as described herein to intermix two separated components of the composition prior to administration, may be useful in the treatment of CPP in a pediatric patient 2 years of age or older, when administered by subcutaneous injection about once every six months (once per six months) to reduce the pediatric patient's peak stimulated blood serum LH concentration to a pre-pubertal concentration level of less than 4 IU/L. According to this embodiment, the syringe device system comprises a first syringe containing an amount of a GnRH agonist or antagonist or a pharmaceutically acceptable salt thereof. In some instances, the syringe device system comprises a first syringe containing an amount of lyophilized leuprolide or a pharmaceutically acceptable salt thereof, such as lyophilized leuprolide acetate. In some instances, the amount of leuprolide or a pharmaceutically acceptable salt thereof in the delivered reconstituted product may be about 42.0 mg leuprolide free base equivalent. In some instances, the amount of leuprolide acetate in the delivered reconstituted product may be about 45.0 mg. According to this embodiment, the syringe device system comprises a second syringe containing an amount of a polymer-solvent system comprising an amount of a biodegradable polymer, which in some instances is a poly(D,L-lactide-co-glycolide) (i.e. PLG) polymer formulation dissolved in a biocompatible solvent, which in some instances is NMP. In some instances, the biodegradable PLG polymer may comprise a lactide to glycolide ratio of about 85:15. In some instances, the PLG polymer may be initiated with hexanediol. In some instances, the PLG polymer may compromise a copolymer containing two primary hydroxyl end groups. In some instances, the PLG polymer may be initiated with dodecanol. In some instances, the PLG polymer may compromise a copolymer containing a hydroxyl end group and an ester end group. In some instances, the PLG polymer has a weight average molecular weight range of about 20 kDa to about 26 kDa. In some instances, the amount of PLG polymer in the delivered reconstituted product may be about 165 mg. In some instances, the amount of NMP in the delivered reconstituted product is about 165 mg.

According to the methods of activating the syringe device system, as disclosed herein, the user, after first allowing the pre-assembled syringe device system to equilibrate to room temperature and then removing it from its packaging, applies force to the user-interface portions 52 and 57 of the displaceable member 50 and the guide member 56, respectively, to activate the syringe coupler from the first closed position to the second open position. The user then applies a force to the second plunger disposed slidably within the second syringe to transfer the polymer-solvent system housed within the internal chamber of the second syringe barrel through the open, activated syringe coupler and into the internal chamber of the first syringe housing the lyophilized leuprolide acetate. Upon contact of the polymer-solvent system with the lyophilized leuprolide acetate, the leuprolide acetate will largely remain in suspension, thus requiring mixing with the polymer-solvent system to ensure that a homogeneous suspension is formed prior to administration. The user then applies a force to the first plunger disposed slidably within the first syringe to transfer the partially to fully mixed components back through the open syringe coupler and into the second syringe. The user will continue mixing the contents back and forth from the first and second syringes, in some instances for about 1 minute, equivalent to approximately 60 full back-and-forth cycles to ensure that the lyophilized leuprolide acetate is fully suspended within the polymer-solvent system. The fully formulated composition is subsequently displaced into the second syringe at a final injection volume of about 0.375 mL and administered formulation weight of about 375 mg. The user then disconnects the second syringe containing the therapeutic formulation from the syringe device by de-threading attachment to the male extension 54 upon the displaceable member 50 of the syringe connector. The user then attaches a needle, for example an 18 G to 20 G needle, to the distal dispensing outlet of the second syringe. The user then subcutaneously administers the full formulation dose to a pediatric patient 2 years of age or older in need of treatment thereof.

According to the methods of administering the GnRH agonist or antagonist or a pharmaceutically acceptable salt thereof to a pediatric patient 2 years of age or older with central precocious puberty (CPP) using the syringe device system disclosed herein, the method comprises subcutaneously administering at least one injection of a pharmaceutic composition comprising a unit dose of a GnRH agonist or antagonist or a pharmaceutically acceptable salt thereof, once every six months (once per six months), to the pediatric patient to reduce the pediatric patient's peak stimulated blood serum LH concentration to a pre-pubertal concentration of less than 4 IU/L. Prior to the administering, the pharmaceutic composition is reconstituted using the syringe device system comprising a first syringe barrel comprising the GnRH agonist or antagonist or a pharmaceutically acceptable salt thereof and a second syringe barrel comprising a liquid formulation component, the first and second syringe barrels being interconnected via a syringe coupler comprising a displaceable seal, wherein the displaceable seal being operable to be axially displaced from a first position to a second position by a force applied to a plunger of the first syringe barrel, and wherein the first position comprises a position in which material transfer through the syringe coupler is occluded, and the second position comprises a position in which at least a portion of the displaceable seal is not secured to an interior surface of the syringe coupler and material transfer through the syringe coupler is permitted. The pharmaceutic composition is reconstituted by applying a force to a user-interface to move the displaceable seal from the first position to the second position and applying force to a plunger positioned in the first syringe barrel and a plunger positioned in the second syringe barrel in an alternating manner to mix contents of the first syringe barrel and the second syringe barrel. In some instances, the GnRH agonist or antagonist or the pharmaceutically acceptable salt thereof is leuprolide or a pharmaceutically acceptable salt thereof, such as leuprolide acetate. In some instances, the pharmaceutical composition comprises about 45 mg of leuprolide acetate and N-methyl-2-pyrrolidone and an 85:15 poly(lactide-co-glycolide) (PLG) copolymer having a weight average molecular weight from about 20 kDa to about 26 kDa and one distal end group that is hydroxyl-terminated and the other distal end group that is either hydroxyl-terminated or ester-terminated as the liquid formulation component.

Various features and embodiments of a pre-connected syringe-to-syringe device and system and methods of using the pre-connected syringe-to-syringe device have been provided herein. It will be recognized, however, that various features are not necessarily specific to certain embodiments and may be provided on any one or more embodiments. The present disclosure and embodiments provided herein are not mutually exclusive and may be combined, substituted, and omitted. The scope of the invention(s) provided herein is thus not limited to any particular embodiment, drawing, or particular arrangement of features.

While various embodiments of the present disclosure have been described in detail, it is apparent that modifications and alterations of those embodiments will occur to those skilled in the art. However, it is to be expressly understood that such modifications and alterations are within the scope and spirit of the present disclosure. Further, the invention(s) described herein are capable of other embodiments and of being practiced or of being carried out in various ways. In addition, it is to be understood that the phraseology and terminology used herein is for the purposes of description and should not be regarded as limiting. The use of "including," "comprising," or "adding" and variations thereof herein are meant to encompass the items listed thereafter and equivalents thereof, as well as, additional items.

What is claimed is:

1. A method for mixing a pharmaceutic composition, comprising:

providing a syringe mixing system, the system comprising a valve assembly with a displaceable member comprising a user-interface and a guide member, wherein the displaceable member is slidable relative to the guide member, and wherein the user-interface is operable to receive a force from a user and transmit the force to a displaceable seal;

a selectively rotatable member operable to receive a syringe;

wherein the valve assembly composes a first position wherein a fluid flow through the assembly is fully occluded, and a second position in which fluid is allowed to flow;

wherein the displaceable member comprises at least one projection in communication with the selectively rotatable member when the displaceable member is in the first position, and wherein the at least one projection is spaced apart from the selectively rotatable member when the displaceable member is in the second position and the selectively rotatable member is freely rotatable when the displaceable member is in the second position;

coupling a first syringe and a second syringe to the valve assembly, wherein the first syringe and the second syringe each comprise a syringe barrel with a hollow body defining an internal chamber, wherein the syringe barrel has a proximal end and a distal dispensing end with an outlet, and a plunger slidably disposed within the hollow body for applying pressure to a syringe content housed within the internal chamber;

displacing the displaceable member relative to the guide member in a direction substantially perpendicular to a longitudinal axis of at least one of the first syringe and the second; and cyclically mixing contents between the first syringe and the second syringe to prepare the contents for delivery to a patient.

2. The method of claim 1, wherein the pharmaceutical composition comprises about 7.5 mg of leuprolide acetate as the active pharmaceutical ingredient and N-methyl-2-pyrrolidone and a 50:50 poly(lactic acid-co-glycolic acid) (PLGA) copolymer having a weight average molecular weight from about 31 kDa to about 45 kDa and at least one terminal carboxylic acid end group as the liquid formulation component.

3. The method of claim 1, wherein the pharmaceutical composition comprises about 22.5 mg of leuprolide acetate as the active pharmaceutical ingredient and N-methyl-2-pyrrolidone, and a 75:25 poly(lactide-co-glycolide) (PLG) copolymer having a weight average molecular weight from about 17 kDa to about 21 kDa and end groups that are hydroxyl-terminated as the liquid formulation component.

4. The method of claim 1, wherein the pharmaceutical composition comprises about 30 mg of leuprolide acetate as the active pharmaceutical ingredient and N-methyl-2-pyrrolidone, and a 75:25 poly(lactide-co-glycolide) (PLG) copolymer having a weight average molecular weight from about 17 kDa to about 21 kDa and one distal end group that is hydroxyl-terminated and the other distal end group that is either hydroxyl-terminated or ester-terminated as the liquid formulation component.

5. The method of claim 1, wherein the pharmaceutical composition comprises about 45 mg of leuprolide acetate as the active pharmaceutical ingredient and N-methyl-2-pyrrolidone, and a 85:15 poly(lactide-co-glycolide) (PLG) copolymer having a weight average molecular weight from about 20 kDa to about 26 kDa and one distal end group that is hydroxyl-terminated and the other distal end group that is either hydroxyl-terminated or ester-terminated as the liquid formulation component.

6. A method for mixing a pharmaceutic composition, comprising:
providing a syringe mixing system, the system comprising a valve assembly with a displaceable member comprising a user-interface and a guide member, wherein the displaceable member is slidable relative to the guide member, and wherein the user-interface is operable to receive a force from a user and transmit the force to a displaceable seal;
wherein the displaceable member comprises at least one resilient projection and the guide member comprises at least one recess for receiving the at least one resilient projection; and
wherein the at least one resilient projection is operable to be displaced upon movement of the displaceable member from a first position and wherein the at least one resilient projection prevents or inhibits the displaceable member from being returned to the first position when it is provided in the at least one recess of the guide member;
coupling a first syringe and a second syringe to the valve assembly, wherein the first syringe and the second syringe each comprise a syringe barrel with a hollow body defining an internal chamber, wherein the syringe barrel has a proximal end and a distal dispensing end with an outlet, and a plunger slidably disposed within the hollow body for applying pressure to a syringe content housed within the internal chamber;
displacing the displaceable member relative to the guide member in a direction substantially perpendicular to a longitudinal axis of at least one of the first syringe and the second; and
cyclically mixing contents between the first syringe and the second syringe to prepare the contents for delivery to a patient.

7. The method of claim 6, wherein the pharmaceutical composition comprises about 7.5 mg of leuprolide acetate as the active pharmaceutical ingredient and N-methyl-2-pyrrolidone and a 50:50 poly(lactic acid-co-glycolic acid) (PLGA) copolymer having a weight average molecular weight from about 31 kDa to about 45 kDa and at least one terminal carboxylic acid end group as the liquid formulation component.

8. The method of claim 6, wherein the pharmaceutical composition comprises about 22.5 mg of leuprolide acetate as the active pharmaceutical ingredient and N-methyl-2-pyrrolidone, and a 75:25 poly(lactide-co-glycolide) (PLG) copolymer having a weight average molecular weight from about 17 kDa to about 21 kDa and end groups that are hydroxyl-terminated as the liquid formulation component.

9. The method of claim 6, wherein the pharmaceutical composition comprises about 30 mg of leuprolide acetate as the active pharmaceutical ingredient and N-methyl-2-pyrrolidone, and a 75:25 poly(lactide-co-glycolide) (PLG) copolymer having a weight average molecular weight from about 17 kDa to about 21 kDa and one distal end group that is hydroxyl-terminated and the other distal end group that is either hydroxyl-terminated or ester-terminated as the liquid formulation component.

10. The method of claim 6, wherein the pharmaceutical composition comprises about 45 mg of leuprolide acetate as the active pharmaceutical ingredient and N-methyl-2-pyrrolidone, and a 85:15 poly(lactide-co-glycolide) (PLG) copolymer having a weight average molecular weight from about 20 kDa to about 26 kDa and one distal end group that is hydroxyl-terminated and the other distal end group that is either hydroxyl-terminated or ester-terminated as the liquid formulation component.

11. A syringe coupler that is operable to receive a first syringe barrel and a second syringe barrel associated with a syringe mixing system, the syringe coupler comprising:
a displaceable member operable to be selectively contacted by a user to convert the syringe coupler from a first position to a second position;
a seal with a flow port that is moveable with the displaceable member;
a first syringe receiving-member and a second syringe-receiving member, wherein at least one of the first syringe-receiving member and the second syringe-receiving member comprises a threaded member;
wherein the displaceable member comprises a projection in selective communication with the threaded member to enable the threaded member to be freely rotatable when the displaceable member is provided in the second position;
wherein the threaded member is substantially prevented from rotating relative to the syringe coupler when the displaceable member is provided in the first position; and
wherein the threaded member is freely rotatable when the displaceable member is provided in the second position.

12. The syringe coupler of claim 11, wherein the first position comprises a closed position in which fluid flow through the coupler is occluded and wherein the second position comprises an open position in which fluid flow through the coupler is enabled.

13. The syringe coupler of claim 11, wherein the threaded member further comprises a contact surface operable to be engaged by a portion of the syringe coupler when the syringe coupler is provided in the first position.

14. The syringe coupler of claim 11, wherein the threaded member comprises a flow port, and wherein the flow port of the seal and the flow port of the threaded member are offset relative to one another in the first position.

15. The syringe coupler of claim 11, wherein the threaded member comprises a flow port, and wherein the flow port of the seal and the flow port of the threaded member are aligned in the second position.

16. The syringe coupler of claim 11, wherein the syringe coupler comprises at least one resilient member to secure the syringe coupler in the second position and substantially prevent the syringe coupler from returning to the first position.

17. The syringe coupler of claim 11, wherein the first syringe receiving-member and the second syringe-receiving member each comprise Luer lock members that are operable to receive a distal end of a syringe.

18. The syringe coupler of claim 11, further comprising a first syringe and a second syringe secured to the syringe coupler, wherein at least one of the first syringe and the second syringe comprises leuprolide or a pharmaceutically acceptable salt thereof.

19. The syringe coupler of claim 11, wherein the displaceable member further comprises at least one resilient projection.

* * * * *